US007256171B1

(12) United States Patent
Marth et al.

(10) Patent No.: US 7,256,171 B1
(45) Date of Patent: Aug. 14, 2007

(54) USE OF CORE 2 G1CNAC TRANSFERASE INHIBITORS IN TREATING INFLAMMATION

(75) Inventors: Jamey D. Marth, San Diego, CA (US); Lesliey G. Ellies, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/856,391

(22) PCT Filed: Nov. 20, 1999

(86) PCT No.: PCT/US99/27465

§ 371 (c)(1),
(2), (4) Date: Jan. 7, 2002

(87) PCT Pub. No.: WO00/31109

PCT Pub. Date: Jun. 2, 2000

(51) Int. Cl.
*A01N 61/00* (2006.01)
*A01N 43/04* (2006.01)
*A01N 25/00* (2006.01)
*A61K 38/16* (2006.01)

(52) U.S. Cl. .................. 514/1; 514/8; 514/23; 514/49; 514/53; 514/54; 514/789

(58) Field of Classification Search .................. 514/1, 514/2, 8, 23, 49, 53, 54, 789; 424/9.1
See application file for complete search history.

(56) References Cited

FOREIGN PATENT DOCUMENTS

| CA | 2186987 A1 | 4/1998 |
|---|---|---|
| WO | WO 97/06176 A2 | 2/1997 |

OTHER PUBLICATIONS

Jain, R.K. et al. Glycobiology, vool. 8, No. 7, pp. 707-717 (1998).*
Hindsgaul, O. et al. J. Biol. Chem. vol. 266, No. 27, pp. 17,858-17,862 (1991).*
Nakamura, M. et al. J. Biol. Chem., vol. 273, No. 41, pp. 26,779-789 (1998).*
Peracchi, A. et al., Rev. Med. Virol., vol. 14, pp. 47-64 (2004).*
Agrawal, S. et al., Molecular Med. Today, vol. 6, pp. 72-81 (2000).*
Chirila, T. et al., Biomaterials, vol. 23, pp. 321-342 (2002).*
Branch, A., Treands in Biochem Sci. (TIBS), vol. 23, pp. 45-50 (1998).*
Elliott, G. et al., Cell, vol. 88, pp. 223-233 (1997).*
Pooga, M. et al., FASEB J., vol. 12, pp. 67-77 (1998).*
Derossi, d. et al., J. Biol. Chem., vol. 289, No. 14, pp. 10,444-10,450 (1994).*
S. Crooke, Antisense Res. and Application, Chapters 1-2, pp. 1-50, Ed. by S. Crooke, Publishers: Springer-Verlag (1998).*
DeClercq, E., Biochem. J., vol. 205, pp. 1-13 (1982).*
Kyung Book Univ., Report Form No. 911-0403-007-2, pp. 1-3 (1991).*

Morin et al., Cancer Res., vol. 43, p. 4 (1983).*
Maaheimo et al., "Synthesis of a divalent sialyl Lewis x O-glycan, a potent inhibitor of lymphocyte-endothelium adhesion evidence that multivalency enhances the saccharide binding to L-section", *Eur. J. Biochem.* 234: 616-625 (1995).
Jain et al., "Inhibition of L- and P-selection by a rationally synthesized novel core 2-like branched structure containing GaINAc-Lewis$^x$ and Neu5Acα2-3Galβ1-3GalNAC", *Glycobiology* 8:7: 707-717 (1998).
Hindsgaul et al., "Evaluation of Deoxygenated Oligosacchararide Acceptor Analogs as Specific Inhibitors of Glycosyltransferases", *The Journal of Biological Chemistry* 266:27: 17858-17862 (1991).
Ellies et al., "Core 2 Oligosaccharide Biosynthesis Distinguishes between Selection Ligands Essential for Leukocyte Homing and Inflammation", *Immunity* 9: 881-890 (1998).
Baum, Linda G. et al.; "Human Thymic Epithelial Cells Express an Endogenous Lectin, Galectin-1, which Binds to Core 2 O-Glycans on Thymocytes and T Lymphoblastoid Cells"; 1995, *J. Exp. Med.*, vol. 181, pp. 877-887.
Bierhuizen, Marti F.A. et al.; "Expression cloning of a cDNA encoding UDP-GlcNAc:Galβ1-3-GalNac-R (GlcNAc to GalNAc) β1-6GlcNAc transferase by gene transfer into CHO cells expressing polyoma Large tumor antigen"; 1992, *Proc. Natl. Acad. Sci:*, vol. 89, pp. 9326-9330.
Brockhausen, I. et al.; "Biosynthesis of O-Glycans in Leukocytes from Normal Donors and from Patients with Leukemia: Increase in O-Glycan Core 2 UDP-GlcNAc:Galβ3GalNAcα-R (GlcNAc to GalNAc) β(1-6)-N-Acetylglucosaminyltransferase in Leukemia Cells" 1991, *Cancer Research*, vol. 51, pp. 1257-1263.
Fox, Robert I. et al.; "A Novel Cell Surface Antigen (T305) Found in Increased Frequency on Acute Leukemia Cells and in Autoimmune Disease States"; 1983, *The Journal of Immunology*, vol. 131, No. 2, pp. 762-767.
Higgins, Elizabeth A. et al.; "Aberrant O-Linked Oligosaccharide Biosynthesis in Lymphocytes and Platelets from Patients with the Wiskott-Aldrich Syndrome"; 1991, *The Journal of Biological Chemistry*, vol. 266, No. 10, pp. 6280-6290.
Kumar, Ravindra et al.; "Core2 β-1,6-N-Acetylglucosaminyltransferase Enzyme Activity Is Critical for P-Selectin Glycoprotein Ligand-1 Binding to P-Selectin"; 1988, *Blood*, vol. 88, No. 10, pp. 3872-3879.
Lasky, Laurence A.; "Selectin-Carbohydrate Interactions and the Initiation of the Inflammatory Response"; 1995, *Annu. Rev. Biochem*, vol. 64, pp. 113-139.
Lowe, John B.; "Selectin ligands, leukocyte trafficking, and fucosyltransferase genes"; 1997, *Kidney International*, vol. 51, pp. 1418-1426.

(Continued)

*Primary Examiner*—Jane Zara
(74) *Attorney, Agent, or Firm*—Townsend & Townsend & Crew

(57) ABSTRACT

This invention provides compounds and methods for treating inflammation. The compounds modulate the core 2 oligosaccharide-mediated binding of inflammatory cells, such as neutrophils, to endothelial cells and other myeloid cells. Significantly, the of the invention methods block inflammation without affecting lymphocyte trafficking. In some embodiments, the compounds inhibit the activity of a core 2 GlcNAc transferase that is involved in synthesizing the core 2 oligosaccharides.

12 Claims, 6 Drawing Sheets

OTHER PUBLICATIONS

Lowe, John B. et al.: "Perspective Series: Cell Adhesion in Vascular Biology"; 1997, *J. Clin. Invest.*, vol. 99, No. 5, pp. 822-826.

Maly, Petr et al.; "The α (1,3) Fucosyltransferase Fuc-TVII Controls Leukocyte Trafficking through an Essential Role in L-, E-, and P-selection Ligand Biosynthesis"; 1996, *Cell*, vol. 86, pp. 643-653.

Piller, Friedrich et al.; "Altered O-Glycan Synthesis in Lymphocytes from Patients with Wiskott-Aldrich Syndrome"; 1991, *J. Exp. Med.*, vol. 173, pp. 1501-1510.

Piller, Friedrich et al.; "Human T-lymphocyte Activation Is Associated with Changes in O-Glycan Biosynthesis" 1991, *The Journal of Biological Chemistry*, vol. 263, No. 29, pp. 15146-15150.

Saitoh, Osamu et al.; "T-Lymphocytic Leukemia Expresses Complex, Branched O-Linked Oligosaccharides on a Mojor Sialoglycoprotein, Leukosialin"; 1991, *Blood*, vol. 77, No. 7, pp. 1491-1499.

Springer, Timothy A.; "Traffic Signals on Endothelium for Lymphocyte Recirculation and Leukocyte Emigration"; 1995, *Annu. Rev. Physiol.*, vol. 57, pp. 827-872.

Tsubol, Shigeru et al.; "Branched O-linked oligosaccharides ectopically expressed in transgenic mice reduce primary T-cell immune responses"; 1997, *The EMBO Journal*, vol. 16, No. 21, pp. 6364-6373.

Williams, David et al.; "Mucin Synthesis: I. Detection in Canine Submaxillary Glands of an N-Acetylglucosaminyltransferase which acts on Mucin Substrates"; 1980, *The Journal of Biological Chemistry*, vol. 255, No. 23, pp. 11247-11252.

* cited by examiner

USE OF CORE 2 G1CNAC TRANSFERASE INHIBITORS IN TREATING INFLAMMATION

BACKGROUND OF THE INVENTION

1. Field of the Invention

This invention pertains to the field of treating inflammation. Compounds and methods for modulating an inflammatory response without significantly affecting lymphocyte trafficking are provided.

2. Background

A mammal often responds to cell injury, infection, or an abrupt change in a tissue by inducing an inflammatory response. Typically, an inflammatory response is initiated by endothelial cells producing molecules that attract and detain inflammatory cells (e.g., myeloid cells such as neutrophils, eosinophils, and basophils) at the site of injury. The inflammatory cells then are transported through the endothelial barrier into the surrounding tissue. The resulting accumulation of inflammatory cells, in particular neutrophils, is followed by generation of toxic oxygen particles and, release of neutrophil granules which contain acid hydrolases and degradative enzymes such as proteases, elastase, and collagenase, which contribute to local tissue breakdown and inflammation. Neutrophils can also release chemoattractants and complement activators that amplify the inflammation.

Although the inflammatory response can play a role in the healing process by destroying, diluting, and isolating injurious agents and stimulating repair of the affected tissue, inflammatory responses can also be harmful, and indeed life-threatening. Five symptoms often characterize the inflammatory response: pain, redness, heat, swelling, and loss of function. For example, inflammation results in leakage of plasma from the blood vessels. Although this leakage can have beneficial effects, it causes pain and when uncontrolled can lead to loss of function and death (such as adult respiratory distress syndrome). Anaphylactic shock, arthritis, and gout are among the conditions that are characterized by uncontrolled or inappropriate inflammation.

Inflammatory responses differ from immune responses mediated by T- and B-lymphocytes in that an inflammatory response is non-specific. While antibodies and MHC-mediated immune responses are specific to a particular pathogen or other agent, the inflammatory response does not involve identification of a specific agent. Both inflammatory responses and specific immune responses, however, involve extravasation of the respective cell types from the blood vessels to the site of tissue injury or infection. Moreover, several of the receptors that mediate extravasation of lymphocytes are also involved in extravasation of inflammatory cells. In particular, lymphocyte trafficking to lymph nodes under normal circumstances is mediated by selectins that are expressed by cells of the vascular endothelium in response to cytokine induction. Selectins are also involved in the recruitment of neutrophils to the vascular endothelium during inflammation (reviewed in Kansas (1996) *Blood* 88: 3259-87; McEver and Cummings (1997) *J. Clin. Invest.* 100: 485-91). Three types of selectins are involved in the interaction between leukocytes and the vascular endothelium. E-selectin (also called endothelial-leukocyte adhesion molecule-1, ELAM-1) and P-selectin are expressed on activated endothelium. P-selectin is also present on activated platelets, while L-selectin is found on lymphocytes. Selectin deficiencies result in varying degrees of impaired lymphocyte trafficking, reduced neutrophil recruitment to sites of inflammation and decreased leukocyte turnover (Arbones et al. (1994) *Immunity* 1: 247-260; Johnson et al. (1995) *Blood* 86: 1106-14; Labow et al. (1995) *Immunity* 1: 709-720; Mayadas et al. (1993) *Cell* 74: 541-554).

Binding of leukocytes to selectins is at least partially mediated by oligosaccharide ligands that are displayed the surface of the cells. The oligosaccharide ligands are generally attached to glycoproteins and glycolipids. The types of oligosaccharides that carry the physiologically relevant selectin ligands are largely undefined at present, with a variety of possibilities existing among N-glycans, O-glycans, glycolipids, as well as proteoglycans (reviewed in Varki (1997) *J. Clin. Invest.* 99: 158-162).

A major ligand for P-selectin is reported to be a protein known as "P-selectin glycoprotein ligand-1" (PSGL-1; Li et al. (1996) *J. Biol. Chem.* 271: 3255-3264; Norgard et al. (1993) *J. Biol. Chem.* 268: 12764-12774). PSGL-1 is a membrane mucin that is disulfide-linked dimer of two 120 kDa subunits. Each subunit of PSGL-1 contains about 70 extracellular serine and threonine residues that are potential sites for O-glycosylation and three potential sites for N-glycosylation (Norgard et al., supra.). Site-directed mutagenesis of PSGL-1 supports a role for tyrosine and threonine residues in the adhesion of PSGL-1 to selecting, thus suggesting that an O-linked glycan is involved (Li et al. (1996) *J. Biol. Chem.* 271: 3255-3264).

Serine/threonine (O)-linked oligosaccharides are diverse structures that are prevalent on cell surfaces and secreted proteins. For example, sulfated, sialylated O-linked oligosaccharides on the high endothelial venules (HEVs) of secondary lymphoid organs are ligands for L-selectin. These ligands are also present on various selectin counter-receptors including CD34 (Baumhueter et al. (1993) *Science* 262: 436-438, GlyCAM-1 (Lasky et al. (1992) *Science* 262: 436-438), MAdCAM-1 (Berg et al. (1993) *Nature* 366: 695-698), Sgp200 (Rosen and Bertozzi (1994) *Curr. Opin. Cell Biol.* 6: 663-673) and the podocalyxin-like protein (Sassetti et al. (1998) *J. Exp. Med.* 187: 1965-1975). Other reported selectin counter-receptors in which O-glycosylation does not appear to be essential include E-selectin ligand-1 (ESL-1)(Steegmaier et al. (1995) *Nature* 373: 615-620), CD24 (Aigner et al. (1995) *Int. Immunol.* 7: 1557-1565), as well as heparin proteoglycans (Norgard-Sumnicht et al. (1993) *Science* 261: 480-483). Moreover, glycolipids contain selectin ligands that function in vitro (Alon et al. (1995) *J. Immunol.* 154: 5356-5366); Larkin et al. (1992) *J. Biol. Chem.* 267: 13661-8); Stroud et al. (1996) *Biochemistry* 35: 758-69).

Widespread expression of C2 GlcNAcT activity among most tissues may explain why the majority of mammalian O-glycans are of the core 2 subtype (FIG. 1)(Brockhausen (1995) "Biosynthesis of O-glycans of the N-acetylgalactosamine-α-Ser/Thr linkage type." In Glycoproteins, Montreull et al., eds. (Elsevier Science) pp. 210-259. Schachter and Brockhausen (1989) *Symp. Soc. Exp. Biol.* 43: 1-26). Core 2 oligosaccharides are common components of mucins, which are glycoproteins for which the majority of their mass is attributable to O-linked oligosaccharides. Mucins are considered to be essential for respiratory epithelium, the gastrointestinal tract and the immune system, by providing a protective function to cell surfaces and regulating cell-cell interactions (reviewed in Hounsell et al. (1996) *Glycoconjugate J.* 13: 19-26; Strous and Dekker (1992) *Crit. Rev. Biochem. Mol. Biol.* 27: 57-92).

Core 2 O-glycans are biantennary and may be diversified by glycosyltransferases that add N-acetylglucosamine (GlcNAc) and galactose (Gal) monosaccharides in β1-3 and β1-4 linkages, thereby generating lactosamine disaccharide repeats termed polylactosamines. These can be further modified with sialic acid (Sia) and L-fucose (Fuc) linked at terminal positions. Such modifications to core 2 O-glycan biosynthesis can provide the oligosaccharide ligands for the selectin family of leukocyte adhesion molecules (FIG. 1)(reviewed in Lasky (1995) *Annu. Rev. Biochem.* 64: 113-139; Lowe (1997) *Kidney Int.* 51: 1418-1426; Springer (1995) *Annu. Rev. Physiol.* 57: 827-72). Both lymphocyte homing and neutrophil recruitment in inflammation require the α1-3 fucosyltransferase VII (FucT-VII) enzyme (Maly et al. (1996) *Cell* 86: 643-653), thus suggesting that a fucosylated oligosaccharide is involved in selectin adhesion. The FucT-VII enzyme can act on N- and O-linked glycans, as well as on glycolipids.

A key branching enzyme that controls O-glycan structural diversity in the synthesis of mammalian O-linked oligosaccharides (O-glycans) is the core 2 β1-6 N-acetylglucosaminyltransferase (C2 GlcNAcT)(Bierhuizen and Fukuda (1992) *Proc. Nat'l. Acad. Sci. USA* 89: 9326-9330); Williams and Schachter (1980) *J. Biol. Chem.* 255: 11247-11252). Kumar et al. reported that transfecting a gene that encodes the core 2 β1-6 N-acetylglucosaminyl-transferase into Chinese hamster ovary (CHO) cells that also express PSGL-1 and the fucosyltransferase resulted in high affinity binding to P selectin (*Blood* (1996) 88: 3872-3879).

Core 2 O-glycan synthesis is also reportedly involved in regulation of lymphoid cell physiology and immune responses (Tsuboi and Fukuda (1997) *EMBO J.* 16: 6364-6373). Antigen-mediated activation of peripheral T and B cells is characterized by upregulation of core 2 GlcNAc-T activity and branched O-glycans on CD43 (Baum et al. (1995) *J. Exp. Med.* 181: 877-887); Pilleretal. (1988) *J. Biol. Chem.* 263: 15146-15150). Core 2 GlcNAc-T has also been implicated in Wiskott-Aldrich Syndrome (WAS)(Higgins et al. (1991) *J. Biol. Chem.* 266: 6280-6290); Piller et al. (1991) *J. Exp. Med.* 173: 1501-1510), AIDS (Fox et al. (1983) *J. Immunol.* 131: 762-7), and leukemia (Brockhausen et al. (1991) *Cancer Res.* 51: 1257-1263; Saitoh et al. (1991) *Blood* 77: 1491-9).

Leukocyte extravasation, lymphocyte trafficking, and other processes thus apparently involve oligosaccharide structures that require core 2 GlcNAc transferase. This has hampered the ability to develop treatments that are effective against chronic and otherwise undesirable inflammation but do not compromise the body's ability to mount an effective defense against pathogens and other agents. Ideally, such treatments would interfere with the inflammatory response at an early stage, while not having an adverse effect on the lymphocyte-mediated immune responses. The present invention fulfills this and other needs.

SUMMARY OF THE INVENTION

The present invention provides methods and compounds for modulating an inflammatory response in a mammal. The modulation is accomplished by administering to the mammal a compound that blocks binding of a core 2 oligosaccharide to a receptor for the core 2 oligosaccharide (e.g., a P-selectin). The core 2 oligosaccharide can be present on an inflammatory cell, such as a neutrophil. In some embodiments, the administration of the compound inhibits binding of the core 2 oligosaccharide to endothelial cells or to other myeloid cells to the inflammatory cells. By targeting core 2 oligosaccharide-mediated binding, the methods are effective against inflammation but do not significantly alter lymphocyte trafficking.

In some embodiments, the methods and compounds of the invention reduce or prevent the synthesis of, a core 2 oligosaccharide. For example, one can administer a compound that inhibits the activity of a core 2 GlcNAc transferase, thus preventing the formation of the core 2 oligosaccharide. For example, the compound can inhibit the enzymatic synthesis of a minimal core 2 oligosaccharide (e.g., prevent the attachment of a β1,6-linked GlcNAc to the Galβ1,3-GlcNAc- acceptor. Other compounds can inhibit the attachment of one or more additional saccharide residues to the minimal core 2 oligosaccharide that would otherwise be added to the core 2 oligosaccharide (e.g., SLe$^x$).

Alternatively, the compound can bind to a core 2 oligosaccharide, thus competing with and inhibiting binding of the core 2 oligosaccharide to the endothelial cells or other myeloid cells that display a receptor (e.g., P-selectin) for the core 2 oligosaccharide.

Also provided by the present invention are methods of modulating the binding of a myeloid cell to an endothelial cell or to a second myeloid cell, the method comprising contacting the myeloid cell with a compound that modulates the synthesis of, a core 2 oligosaccharide on the surface of the myeloid cell. Alternatively, the accessibility of the compound can bind to the core 2 oligosaccharide, thus reducing the ability of the core 2 oligosaccharide to bind to a corresponding receptor. Myeloid cells of interest include, for example, neutrophils, eosinophils, monocytes, and granulocytes.

The invention also provides methods of identifying a compound for use in inhibiting an inflammatory response in a mammal. These methods involve: a) providing an assay mixture which comprises: a core 2 GlcNAc transferase, a potential inflammation modulator, a UDP-GlcNAc sugar donor, an acceptor saccharide, and additional reagents required for core 2 GlcNAc transferase activity; b) incubating the assay mixture under conditions in which the core 2 GlcNAc transferase is active; and c) determining whether the amount of GlcNAc transferred to the acceptor saccharide is increased or decreased in comparison to an assay which lacks the potential inflammation modulator. A potential inflammation modulator which results in a decrease in GlcNAc transfer to the acceptor saccharide is suitable for inhibiting an inflammatory response.

Additional methods for identifying lead compounds that can be further tested to identify those that are useful for inhibiting an inflammatory response in a mammal are also provided. These methods involve: a) providing a cell which comprises a polynucleotide that encodes a core 2 GlcNAc transferase, an acceptor saccharide for the core 2 GlcNAc transferase, and UDP-GlcNAc; b) contacting the cell with a potential inflammation modulator and incubating the cell under conditions in which the core 2 GlcNAc transferase is normally expressed; and c) determining whether the core 2 oligosaccharide level is increased or decreased compared to the core 2 oligosaccharide level in the absence of the potential inflammation modulator. A potential inflammation modulator that causes a decrease in the amount of core 2 oligosaccharide produced is suitable for further testing to determining whether the compound inhibits an inflammatory response in a mammal. The cell used in the assay can, in some embodiments, contain one or more glycosyltransferases in addition to the core 2 GlcNAc transferase, as well as corresponding reactants (e.g., nucleotide sugars), that can add additional saccharide residues to the GlcNAc of a minimal core 2 oligosaccharide to form a modified core 2 oligosaccharide. In these embodiments, the level of core 2 oligosaccharide is determined by detecting the presence or absence of the modified core 2 oligosaccharide.

Lead compounds that potentially inhibit inflammation in a mammal but do not inhibit lymphocyte-mediated immune responses can also be identified by contacting a library of potential inflammation modulator compounds with a core 2 oligosaccharide and identifying potential inflammation modulator compounds that bind to the core 2 oligosaccharide. A compound that binds to the core 2 oligosaccharide is a lead compound suitable for further testing as an inflammation modulator.

BRIEF DESCRIPTION OF THE DRAWINGS

In FIG. 2A, the wild type C2GlcNAcT genomic locus was used in conjunction with the pflox vector to construct a targeting vector in which the single exon open reading frame was flanked by loxP sites (C2 GlcNAcT$^{F[kneo]}$). Restriction enzyme sites indicated are Bam HI (B), Bgl II (Bg), Hind III (H), Not I (N), and Xba I (X). Transient Cre expression in C2 GlcNAcT-targeted ES cells resulted in subclones isolated with a C2 GlcNAcT$^{\Delta}$ (systemic-null) or C2 GlcNAcT (conditional-null) mutation (FIG. 2B). FIG. 2C shows a Southern blot analysis of a Bam HI/Bgl II digest of ES cell DNA probed with a loxP probe, which confirmed the expected structures. Wild type RI ES cell DNA showed no hybridization with the loxP probe. Three loxP sites are present in a targeted parental clone (156), one loxP site is present in each of two C2 GlcNAcT$^{\Delta}$ subclones (156.24 and 156.29) and two loxP sites are present in the C2 GlcNAcT$^{F}$ subclone (156.34). In the right panel, tail DNA from a heterozygous mating of progeny from a C2 GlcNAcT$^{\Delta}$ chimera digested with Hind III and probed with the genomic probe indicates the 6.5 kb wild type allele and the 3.7 kb mutant allele.

In FIG. 3A, tissues normally expressing C2 GlcNAcT activity were assayed for enzyme activity in wild type, heterozygous and homozygous null mice. Results represent one of three similar experiments. FIG. 3B shows an oligosaccharide analysis that was carried out on splenocytes of wild type and C2 GlcNAcT$^{\Delta/\Delta}$ mice. [$^{3}$H]-Glucosamine labeled O-glycans were isolated and subjected to Bio-Gel P-4 gel filtration (upper panels). The fractions containing sialylated oligosaccharides (peaks 1 and 2) were combined, desialylated and subjected to HPLC (lower panels). Peaks 1, 2, 3, 4, and 5 indicate the elution positions of disialylated forms of Gall 1-3(Galβ1-4GlcNAcβ1-6)GalNAcOH and Galβ1-3GalNAcOH (peak 1) and monosialylated forms of Gall 1-3(Galβ1-4GlcNAcβ1-6)GalNAcOH and Galβ1-3GalNAcOH (peak 2), Galβ1-3(Gal 1-4GlcNAcβ1-6)GalNAcOH (peak 3), Galβ1-3GalNAcOH (peak 4) and GalNAcOH (peak 5). In the experiment shown in FIG. 3C, splenocytes were double-stained with mAbs recognizing CD22 and the B cell specific form of CD45 (B220) or CD22 and all CD45 isoforms (30-F11). Cells were also double-stained with mAbs recognizing the 115 (S7) and 130 (1B11) kD glycoforms of CD43 and subjected to flow cytometric analysis. Myeloid cells were gated by forward and side scatter.

FIG. 5A: Purified peripheral blood leukocytes were stained with Gr-1 and either the P- or E-selectin-IgM chimera for 30 min at 4° C. A goat anti human secondary was used to detect the IgM chimeras and live cells were gated on the Gr-1 positive population when subjected to FACS analysis. Cells stained in the presence of EDTA acted as the controls. Data are representative of 4 separate experiments. FIG. 5B: Peripheral blood leukocytes were stained with Gr-1 and monoclonal or polyclonal antibodies directed against leukocyte adhesion molecules (CD11a, CD11b, CD18) or the selectin counter-receptors (CD24, CD62L, PSGL-1). The panel is 1 of 3 similar experiments in which data collected represents 2500 events gated on Gr-1 positive cells.

FIG. 6A: Mesenteric and peripheral (brachial and axillary) lymph nodes and Peyer's patch aggregates were isolated from wild type or C2 GlcNAcT null mice. Lymphocytes recovered from each organ were quantitated manually using a hemocytometer. Seven animals of each genotype were analyzed and results are presented as means ±SEM. Frozen sections of peripheral lymph nodes stained with hematoxylin and eosin were photographed at 25× magnification. FIG. 6B: For L-selectin immunohistochemistry, frozen sections of peripheral lymph nodes from wild type (left panels) or C2 GlcNAcT$^{\Delta/\Delta}$ (right panels) mice were stained with an L selectin IgM immunohistochemical probe or with the MECA 79 antibody. FIG. 6C: In lymphocyte homing studies, wild type lymphocytes were injected into the tail vein of wild type or C2 GlcNAcT null mice. CMFDA positive lymphocytes in mesenteric and peripheral (brachial and axillary) lymph nodes, and Peyer's patches from four mice of each genotype were analyzed by flow cytometry (100,000 events). Data are presented as the mean ±the SEM. The slight decrease in homing to Peyer's patch tissue was not statistically significant (p=0.38).

DETAILED DESCRIPTION

Definitions

The following abbreviations are used herein:

| | |
|---|---|
| Ara = | arabinosyl; |
| Fru = | fructosyl; |
| Fuc = | fucosyl; |
| Gal = | galactosyl; |
| GalNAc = | N-acetylgalactosaminyl; |
| Glc = | glucosyl; |
| GlcNAc = | N-acetylglucosaminyl; |
| Man = | mannosyl; and |
| NeuAc = | sialyl(N-acetylneuraminyl). |

Oligosaccharides are considered to have a reducing end and a non-reducing end, whether or not the saccharide at the reducing end is in fact a reducing sugar. In accordance with accepted nomenclature, oligosaccharides are depicted herein with the non-reducing end on the left and the reducing end on the right. All oligosaccharides described herein are described with the name or abbreviation for the non-reducing saccharide (e.g., Gal), followed by the configuration of the glycosidic bond ($\alpha$ or $\beta$), the ring bond, the ring position of the reducing saccharide involved in the bond, and then the name or abbreviation of the reducing saccharide (e.g., GlcNAc). The linkage between two sugars may be expressed, for example, as 2,3, 2→3, or (2,3). Each saccharide is a pyranose.

Figure 1:
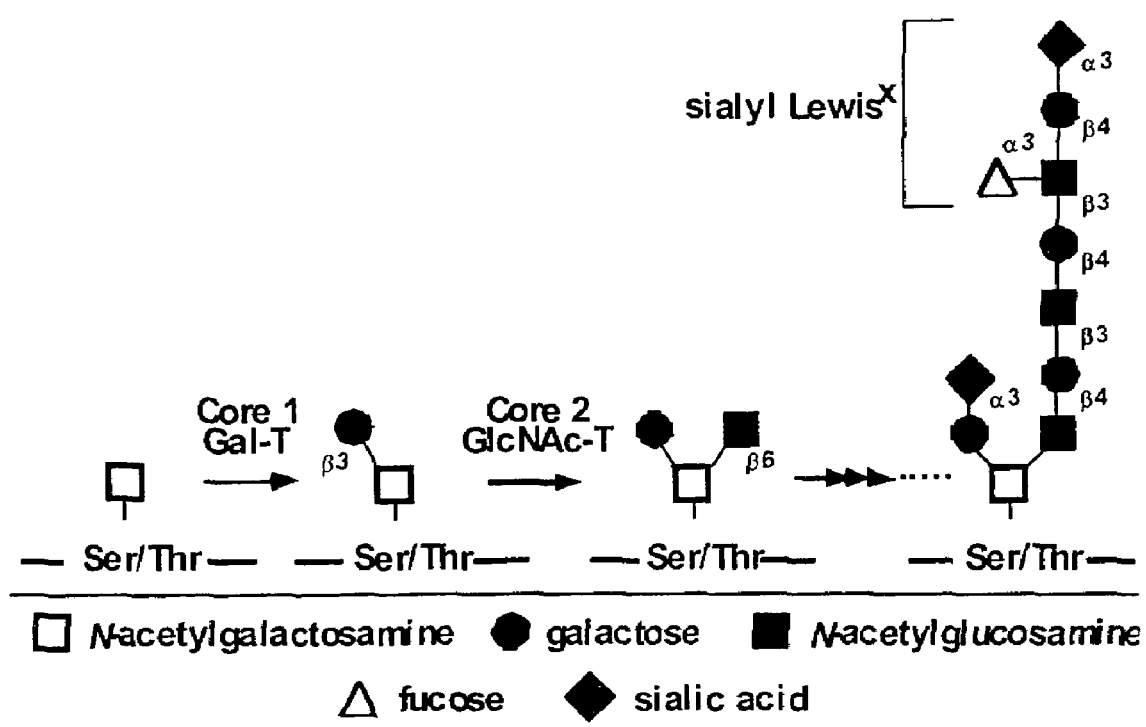
FIG. 1 shows a diagram of mammalian O-glycan biosynthesis, specifically the production of Core 1 and Core 2 O-glycans. The core 2 GlcNAcT enzyme functions in generating bi-antennary O-glycans in the Golgi. The core 2 branch provides a scaffold for the subsequent production of lactosamine disaccharide repeats and the selectin ligand sialyl Lewis X.

A "core 2 oligosaccharide" is an O-linked, branched saccharide moiety, the biosynthesis of which requires the activity of a core 2 GlcNAc$\beta$1,6-transferase. Generally, a core 2 oligosaccharide includes, at minimum, a GalNAc residue to which is attached a galactose ($\beta$1,3- or $\beta$1,4-linked) and a GlcNAc residue ($\beta$1,6-linked to the GalNAc) (FIG. 1). The core 2 GlcNAc transferase is the enzyme that catalyzes the attachment of the GlcNAc residue to form this "minimal core 2 oligosaccharide." A core 2 oligosaccharide can also have additional carbohydrate residues attached to either or both of the galactose and GlcNAc residues, as shown in FIG. 1. The GlcNAc branch can serve as a scaffold for the addition of polylactosamine, sialyl Lewis$^x$ (SLe$^x$), and other saccharide structures; such "modified core 2 oligosaccharides" are also considered to fall within the meaning of the term core 2 oligosaccharides, as is used herein. The initial GalNAc residue is generally O-linked to a hydroxyl group that is present on, for example, a serine or threonine residue of a polypeptide, a glycolipid, or other hydroxylated molecule.

Much of the nomenclature and general laboratory procedures required in this application can be found in Sambrook, et al., *Molecular Cloning: A Laboratory Manual* (2nd Ed.), Vol. 1-3, Cold Spring Harbor Laboratory, Cold Spring Harbor, N.Y., 1989. The manual is hereinafter referred to as "Sambrook et al."

The term "nucleic acid" refers to a deoxyribonucleotide or ribonucleotide polymer in either single- or double-stranded form, and unless otherwise limited, encompasses known analogues of natural nucleotides that hybridize to nucleic acids in manner similar to naturally occurring nucleotides. Unless otherwise indicated, a particular nucleic acid sequence includes the complementary sequence thereof.

An "inhibitory nucleic acid" is any nucleic acid or modified nucleic acid used or designed for use in inhibitory nucleic acid therapy. "Inhibitory nucleic acid therapy" refers to the use of inhibitory nucleic acids to inhibit gene expression, for example, inhibition of DNA transcription, inhibition of RNA processing, transport or translation, or inhibition of protein synthesis. Inhibitory nucleic acid therapy includes the variety of approaches for treatment of disease using nucleic acids or modified nucleic acids as described herein. Various inhibitory nucleic acid therapies, including antisense nucleic acids, are discussed in detail below.

The term "operably linked" refers to functional linkage between a nucleic acid expression control sequence (such as a promoter, signal sequence, or array of transcription factor binding sites) and a second nucleic acid sequence, wherein the expression control sequence affects transcription and/or translation of the nucleic acid corresponding to the second sequence.

The term "recombinant" when used with reference to a cell indicates that the cell replicates a heterologous nucleic acid, or expresses a peptide or protein encoded by a heterologous nucleic acid. Recombinant cells can contain genes that are not found within the native (non-recombinant) form of the cell. Recombinant cells can also contain genes found in the native form of the cell wherein the genes are modified and re-introduced into the cell by artificial means. The term also encompasses cells that contain a nucleic acid endogenous to the cell that has been modified without removing the nucleic acid from the cell; such modifications include those obtained by gene replacement, site-specific mutation, and related techniques.

A "heterologous sequence" or a "heterologous nucleic acid", as used herein, is one that originates from a source foreign to the particular host cell, or, if from the same host cell, is modified from its original form.

A "subsequence" refers to a sequence of nucleic acids or amino acids that comprise a part of a longer sequence of nucleic acids or amino acids (e.g., polypeptide) respectively.

A "recombinant expression cassette" or simply an "expression cassette" is a nucleic acid construct, generated recombinantly or synthetically, that includes nucleic acid elements that are capable of affecting expression of a structural gene in hosts that are compatible with such sequences. Expression cassettes include at least promoters and optionally, transcription termination signals. Typically, the recombinant expression cassette includes a nucleic acid to be transcribed (e.g., a nucleic acid encoding a desired polypeptide), and a promoter. Additional factors necessary or helpful in effecting expression may also be used as described herein. For example, an expression cassette can also include nucleotide sequences that encode a signal sequence that directs secretion of an expressed protein from the host cell. Transcription termination signals, enhancers, and other nucleic acid sequences that influence gene expression, can also be included in an expression cassette.

The term "isolated" is meant to refer to material which is substantially or essentially free from components which normally accompany the enzyme or other material of interest as found in its native state. Thus, the enzymes, nucleic acids, or other materials of the invention, when isolated, do not include materials normally associated with their in situ environment. Typically, isolated proteins or nucleic acids are at least about 80% pure, usually at least about 90%, and preferably at least about 95% pure as measured by standard methods, such as by determining band intensity on a silver stained gel or other method for determining purity. Protein and nucleic acid purity or homogeneity can be indicated by a number of means well known in the art, such as polyacrylamide gel electrophoresis of a protein sample, followed by visualization upon staining. For certain purposes high resolution will be needed and HPLC or a similar means for purification utilized.

The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence, as measured using one of the following sequence comparison algorithms or by visual inspection.

The phrase "substantially identical," in the context of two nucleic acids or polypeptides, refers to two or more sequences or subsequences that have at least 70%, preferably 80%, most preferably 90-95% nucleotide or amino acid residue identity, when compared and aligned for maximum correspondence, as measured using one of the following sequence comparison algorithms or by visual inspection. Preferably, the substantial identity exists over a region of the sequences that is at least about 50 residues in length, more preferably over a region of at least about 100 residues, and most preferably the sequences are substantially identical over at least about 150 residues. In a most preferred embodiment, the sequences are substantially identical over the entire length of the coding regions.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., supra).

Another example of algorithm that is suitable for determining percent sequence identity and sequence similarity is the BLAST algorithm, which is described in Altschul et al., *J. Mol. Biol.* 215:403-410 (1990). Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89:10915 (1989)).

In addition to calculating percent sequence identity, the BLAST algorithm also performs a statistical analysis of the similarity between two sequences (see, e.g., Karlin & Altschul, *Proc. Nat.'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences or polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions, as described below.

"Bind(s) substantially", in the context of nucleic acids, refers to complementary hybridization between a probe nucleic acid and a target nucleic acid and embraces minor mismatches that can be accommodated by reducing the stringency of the hybridization media to achieve the desired detection of the target polynucleotide sequence.

The phrase "hybridizing specifically to", refers to the binding, duplexing, or hybridizing of a molecule only to a particular nucleotide sequence under stringent conditions when that sequence is present in a complex mixture (e.g., total cellular) DNA or RNA. The term "stringent conditions" refers to conditions under which a probe will hybridize to its target subsequence, but to no other sequences. Stringent conditions are sequence-dependent and will be different in different circumstances. Longer sequences hybridize specifically at higher temperatures. Generally, stringent conditions are selected to be about 5° C. lower than the thermal melting point (Tm) for the specific sequence at a defined ionic strength and pH. The Tm is the temperature (under defined ionic strength, pH, and nucleic acid concentration) at which 50% of the probes complementary to the target sequence hybridize to the target sequence at equilibrium (as the target sequences are generally present in excess, at Tm, 50% of the probes are occupied at equilibrium). Typically, stringent conditions will be those in which the salt concentration is less than about 1.0 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C.

for long probes (e.g., greater than 50 nucleotides). Stringent conditions may also be achieved with the addition of destabilizing agents such as formamide.

The phrases "specifically binds" refers to a binding reaction which is determinative of the presence of the target molecule in the presence of a heterogeneous population of proteins, saccharides and other biologics. Thus, under designated assay conditions, the specified receptors or other compounds bind preferentially to a core 2 oligosaccharide or other molecule of interest and do not bind in a significant amount to other molecules present in the sample. Specific binding to a protein under such conditions requires a receptor that is selected for its specificity for a particular ligand. A variety of assay formats can be used to select receptors that are specifically reactive with a particular ligand. For example, solid-phase ELISA immunoassays are routinely used to select monoclonal antibodies that are specifically immunoreactive with a core 2 oligosaccharide or other molecule. See, Harlow and Lane (1988) *Antibodies, A Laboratory Manual*, Cold Spring Harbor Publications, New York, for a description of immunoassay formats and conditions that can be used to determine specific immunoreactivity.

"Conservatively modified variations" of a particular polynucleotide sequence refers to those polynucleotides that encode identical or essentially identical amino acid sequences, or where the polynucleotide does not encode an amino acid sequence, to essentially identical sequences. Because of the degeneracy of the genetic code, a large number of functionally identical nucleic acids encode any given polypeptide. For instance, the codons CGU, CGC, CGA, CGG, AGA, and AGG all encode the amino acid arginine. Thus, at every position where an arginine is specified by a codon, the codon can be altered to any of the corresponding codons described without altering the encoded polypeptide. Such nucleic acid variations are "silent substitutions" or "silent variations," which are one species of "conservatively modified variations." Every polynucleotide sequence described herein which encodes a polypeptide also describes every possible silent variation, except where otherwise noted. Thus, silent substitutions are an implied feature of every nucleic acid sequence which encodes an amino acid. One of skill will recognize that each codon in a nucleic acid (except AUG, which is ordinarily the only codon for methionine) can be modified to yield a functionally identical molecule by standard techniques. In some embodiments, the nucleotide sequences that encode the enzymes are preferably optimized for expression in a particular host cell (e.g., yeast, mammalian, plant, fungal, and the like) used to produce the enzymes.

Similarly, "conservative amino acid substitutions," in one or a few amino acids in an amino acid sequence are substituted with different amino acids with highly similar properties are also readily identified as being highly similar to a particular amino acid sequence, or to a particular nucleic acid sequence which encodes an amino acid. Such conservatively substituted variations of any particular sequence are a feature of the present invention. Individual substitutions, deletions or additions which alter, add or delete a single amino acid or a small percentage of amino acids (typically less than 5%, more typically less than 1%) in an encoded sequence are "conservatively modified variations" where the alterations result in the substitution of an amino acid with a chemically similar amino acid. Conservative substitution tables providing functionally similar amino acids are well known in the art. See, e.g., Creighton (1984) *Proteins*, W.H. Freeman and Company.

The term "sialic acid" refers to any member of a family of nine-carbon carboxylated sugars. The most common member of the sialic acid family is N-acetyl-neuraminic acid (2-keto-5-acetamindo-3,5-dideoxy-D-glycero-D-galactononulopyranos-1-onic acid (often abbreviated as Neu5Ac, NeuAc, or NANA). A second member of the family is N-glycolyl-neuraminic acid (Neu5Gc or NeuGc), in which the N-acetyl group of NeuAc is hydroxylated. A third sialic acid family member is 2-keto-3-deoxy-nonulosonic acid (KDN)(Nadano et al. (1986) *J. Biol. Chem.* 261: 11550-11557; Kanamori et al. (1990) *J. Biol. Chem.* 265: 21811-21819. Also included are 9-substituted sialic acids such as a 9-O—C1-C6 acyl-Neu5Ac like 9-O-lactyl-Neu5Ac or 9-O-acetyl-Neu5Ac, 9-deoxy-9-fluoro-NeuSAc and 9-azido-9-deoxy-Neu5Ac. For review of the sialic acid family, see, e.g., Varki (1992) *Glycobiology* 2: 25-40; *Sialic Acids: Chemistry, Metabolism and Function*, R. Schauer, Ed. (Springer-Verlag, New York (1992). The synthesis and use of sialic acid compounds in a sialylation procedure is disclosed in international application WO 92/16640, published Oct. 1, 1992.

The term "transgenic" refers to a cell that includes a specific genetic modification that was introduced into the cell, or an ancestor of the cell. Such modifications can include one or more point mutations, deletions, insertions, or combinations thereof. When referring to an animal, the term "transgenic" means that the animal includes cells that are transgenic, and descendants of such animals. An animal that is composed of both transgenic and non-transgenic cells is referred to herein as a "chimeric" animal.

DESCRIPTION OF THE PREFERRED EMBODIMENTS

The present invention provides methods and compounds that are suitable for modulating binding of a first myeloid cell to an endothelial cell or to a second myeloid cell. Such methods and compounds can be used to prevent or reduce an inflammatory response in a mammal. Unlike previously available methods for modulating inflammation, the methods and compounds of the invention are specific for inflammation and do not interfere with B- and T-lymphocyte-mediated immune responses. Also provided are screening methods for identifying compounds that are useful for modulating binding of a first myeloid cell to an endothelial cell or to a second myeloid cell. Such compounds are suitable for use as lead compounds to further test for ability to reduce or treat inflammation. Transgenic animals that lack a functional gene for the core 2 GlcNAc transferase are also provided by the invention.

The compounds and methods of the invention are useful not only for therapeutic and drug discovery use, but also for studies of the effect on the inflammation process of different cell types and their interaction.

The invention is based in part upon the discovery that the binding of inflammatory cells to the blood vessel endothelium, and extravasation of the inflammatory cells from the blood vessel to the tissue, is mediated by core 2 oligosaccharides. Surprisingly, the trafficking of lymphocytes from the blood to a site of infection or tissue damage is not affected by the absence of core 2 oligosaccharides, even though extravasation of lymphocytes and cells involve similar receptors. Accordingly, the methods of the invention involve administering to a mammal a therapeutically effective amount of a compound that can modulate the core 2 oligosaccharide-mediated binding of an inflammatory cell to a receptor for the core 2 oligosaccharide. The compound can reduce the synthesis of, or enhance the degradation of, a core 2 oligosaccharide, thus resulting in a reduction in trafficking of inflammatory cells to a potential site of inflammation. A reduction in the amount and/or binding availability of the core 2 oligosaccharide thus causes a reduction of the transfer of inflammatory cells to a potential site of inflammation. Lymphocyte trafficking, however, is not affected by the loss or blocking of the core 2 oligosaccharide.

The methods and compositions of the invention alter the amount of core 2 oligosaccharide that is present and available for binding on various cell types, particularly inflammatory cells such as neutrophils. The core 2 oligosaccharide can be present on any of several glycoconjugates such as, for example, glycoproteins or glycolipids. When attached to a glycoprotein, the core 2 oligosaccharide is generally linked to the protein through an O linkage to a threonine or serine residue. The core 2 glycan, which has the structure Galβ1→3(GlcNAcβ1→6) GalNAc- (FIG. 1), can be attached directly to an O residue of a glycoprotein, or can be attached to a saccharide residue that is attached to the glycoprotein or glycolipid. One example of a glycolipid-associated core 2 oligosaccharide is Galβ1→3 (GlcNAcβ1→6) GalNAcβ1→3Galα1→4Galβ1→4Glcβ1→lipid (e.g., ceramide). Another example is a glycolipid in which the core 2 structure is linked by an α1→3 linkage to another saccharide residue.

In some embodiments, the methods of the invention cause a change in the activity of the core 2 GlcNAc transferase (E.C. 2.4.102), which is also referred to as core 2 β-1,6-N-acetylglucosaminyltransferase (C2 GlcNAc-T). This enzyme catalyzes the transfer of GlcNAc from the activated sugar UDP-GlcNAc to an acceptor saccharide that includes the structure Galβ1→3GalNAc-. Thus, for example, the invention relates to blocking agents that inhibit the activity of C2 GlcNAc-T. The blocking agents of the invention can act directly on the enzyme or substrate for the enzyme, or can inhibit expression of a gene that encodes the enzyme. Alternatively, one can administer an agent that destroys the core 2 oligosaccharide by, for example, converting the structure into an oligosaccharide that cannot be bound by a ligand on, for example, an endothelial cell of a second myeloid cell. Blocking agents, such as antibodies, that bind to the core 2 oligosaccharide and thus prevent binding by the ligands can also be administered according to the methods of the invention.

Methods are also disclosed for preparing the inflammation modulating agents as well as various screening assays to identify suitable candidates. Therapeutic and other uses for these compounds are also provided.

I. Methods for Modulating Core 2 Oligosaccharide-Mediated Inflammatory Cell Binding and Extravasation The present invention provides methods for modulating the binding of cells that are involved in inflammation to endothelial cells and also to other endothelial cells. This binding is mediated by a core 2 oligosaccharide that is displayed on the surface of inflammatory cells such as neutrophils. Endothelial cells, and other cells to which neutrophils bind, display a receptor for the core 2 oligosaccharide. In at least some cases, this receptor is a selectin such as P- or E-selectin. By modulating this intercellular binding, an inflammatory response can be prevented or treated.

A. Inhibitors of Glycosyltransferases Involved in Synthesis of Core 2 Oligosaccharides In one embodiment, the methods involve reducing or preventing inflammation by inhibiting the enzymatic activity of glycosyltransferase polypeptides that are involved in synthesis of the core 2 oligosaccharides. Glycosyltransferases, the general group of enzymes that catalyze the synthesis of these moieties, catalyze the transfer of a monosaccharide from a glycosylnucleotide (the donor substrate) to an acceptor substrate. The acceptor substrate may be another glycosyl residue, a polypeptide, or a lipid, depending on the specificity of the transferase. See, e.g., Beyer et al. (1981) *Adv. in Enzym.* 52: 24. Glycosyltransferases are grouped into families based on the type of sugar residue transferred. For example, enzymes that transfer sialic acid are called sialyltransferases, those that transfer fucose are called "fucosyltransferases," and those that transfer sialic acids are termed "sialyltransferases." Sialyltransferases are a family of glycosyltransferase enzymes that add sialic acid residues during oligosaccharide diversification (for review, see, e.g., Harduin-Lepers et al. (1995) *Glycobiology* 5: 741-758). Sialic acid addition occurs in the Golgi apparatus and generally terminates further oligosaccharide chain elongation. In each family there are typically 10-15 different enzymes required to elaborate the diverse carbohydrate structures found on glycoproteins and glycolipids of animal cells. Each enzyme makes a defined structure based on the donor and acceptor substrates they utilize, and the anomeric linkage formed in the transfer reaction.

Preferably, the inhibitor is specific for the particular glycosyltransferase of interest, and the glycosyltransferase is one that is not required for synthesis of other oligosaccharides that are not involved in an inflammatory response. In preferred embodiments, the target glycosyltransferase is a C2 GlcNAc transferase, as this enzyme is involved almost exclusively in the synthesis of core 2 oligosaccharides and is not involved in the synthesis of other oligosaccharides.

Having identified the target enzyme to be inhibited (e.g., a C2 GlcNAc-T), many approaches can be used to block its activity. Examples of agents capable of inhibiting enzyme activity include, immunoglobulins, suicide substrates, alkylating agents, and various substrate analogs. For a review, see Fersht, *Enzyme Structure and Mechanism* (2d ed. 1985). The methods of modulating inflammation by inhibiting glycosyltransferase activity can involve administering to a mammal a compound that is an analog of a substrate for the glycosyltransferase.

In some embodiments, the inhibitor is a sugar nucleotide or an analog of a donor substrate, e.g., an analog of GlcNAc or UDP-GlcNAc. As discussed above, the donor substrate of glycosyltransferases are sugar nucleotides, usually diphosphonucleosides. For example, uridine diphosphosugars are donor substrates for the formation of glycosides of glucose, galactose, N-acetylglucosamine, xylose, and glucuronic acid. Guanosine diphosphosugars are donor substrates for the synthesis of glycosides of mannose and fucose.

Using this knowledge, one of skill in the art can readily synthesize a number of sugar nucleotides which can then be tested to identify those capable of maximum inhibition of a specific enzyme. The term "sugar nucleotide" as used herein refers both to sugar nucleotides discussed above and to various analogs thereof that might be synthesized or isolated from natural sources. The number of variations on this structure is limitless. For instance, both the ester linkage between the sugar and phosphate and the anhydride linkage of the pyrophosphate are potential targets of enzymatic cleavage. Replacement of the O—P or C—O linkage with a more stable C—P bond provides nucleotide monophosphate or diphosphate sugar analogs that are more resistant to enzymatic degradation. Such compounds have the potential to selectively inhibit glycoprotein or glycolipid synthesis by acting as substrate analogs of a particular glycosyltransferase. See, e.g., Vaghefi et al., *J. Med. Chem.* 30:1383-1391 (1987), and Vaghefi et al., *J. Med. Chem.* 30:1391-1399 (1987). Glycosyltransferase inhibitors are also described, for example, in U.S. Pat. No. 5,461,143.

Another approach is to replace the monophosphate or diphosphate bridge between the sugar residue and the nucleoside moiety. For instance, the diphosphate bridge can be replaced with an isosteric —OCONHSO$_2$O— residue. See, Samarasa, et al., *J. Med. Chem.* 28:40-46 (1985).

Analogs of sugar nucleotides capable of inhibiting glycosylation have been used as antibiotics and antiviral agents. Examples of such compounds include 2-deoxy-D-glucose, which is transformed to either UDP-2dGlc or GDP-2dGlc and in that form inhibits glycosylation of glycoproteins in the viral envelope. DeClercq, *Biochem. J.* 205:1 (1982) which is incorporated herein by reference. Antibiotics such as tunicamycin and streptovirudin are also effective because of their ability to inhibit glycosylation. For instance, tunicamycin is an analog of UDP-GlcNAc, the donor substrate for N-acetylglucos-aminyltransferases. The replacement of diphosphate bridge with a carbon chain allows tunicamycin to cross the cell membrane but still readily bind the active site of the enzyme. The structure of these and related compounds provide one of skill in the art with direction in designing and synthesizing compounds with similar inhibitory effects in accordance with the present invention as described herein.

Nucleotides are the byproduct of the reaction by which glycosyl residues are transferred to acceptor substrates. Nucleotides have been found to competitively inhibit glycosyltransferase. Thus, various nucleotides and their analogs have potential as inhibitors of these enzymes. For example, UDP and UMP can be used to inhibit C2 GlcNAc-T activity.

In addition to the donor substrate analogs, analogs of acceptor substrates may also be used as inhibitors. Again, the skilled artisan will recognize a variety of possible structures that can be used. Because of the acceptor substrate specificity of C2 GlcNAc-T, specific inhibition of the C2 GlcNAc-T can be achieved. Ideally, the inhibitory compounds should be capable of acting as specific acceptor substrates for a given enzyme, even in the presence of other enzymes. In addition, the compound should be an efficient acceptor substrate. Thus, the $K_i$ of the inhibitor should be at least about $10^{-5}$ M, more preferably at least about $10^{-7}$ M. Suitable analogs for inhibition of the C2 GlcNAc-T include derivatives of Galβ1→3GalNAc- in which the galactose residue is replaced by 6-deoxygalactose. The deoxygalactose-containing compounds bind to the C2 GlcNAc-T, but do not function as an acceptor.

Glycosyltransferases can also be inhibited by contacting acceptor substrates for the glycosyltransferase with a competing glycosyltransferase or glycosidase that converts the acceptor oligosaccharide into a different structure that does not function as an acceptor for the glycosyltransferase of interest. For example, one can inhibit C2 GlcNAc-T activity by contacting a Galβ1→3GalNAc-containing oligosaccharide with an α2,6 sialyltransferase (ST6 GalNAc II), which forms the oligosaccharide structure Galβ1→3(Siaα2→6-)GalNAc, which is not utilized by C2 GlcNAc-T as an acceptor substrate. Other sialyltransferases are also suitable for this purpose; these include, for example, ST3Gal I, ST6GalNAcs I, III, and IV, and others that can utilize a GalNAc residue as an acceptor. Photoreactive nitrophenyl substrate derivatives are another example of an effective inhibitor of C2 GlcNAc-T (Toki et al. (1994) *Biochein. Biophys. Res. Commun.* 198: 417-423).

Naturally occurring molecules which show inhibitory effects can also be isolated for use in the present invention. The biosynthesis of glycoproteins or glycolipids is a complex metabolic pathway that depends on many factors for regulation. Naturally occurring inhibitory compounds can be purified and used to further inhibit activity.

The preferred glycosyltransferase inhibitors of the present invention have the ability to cross the cell membrane and enter the Golgi apparatus. Thus, the blocking agents are preferably sufficiently hydrophobic to allow diffusion through the membrane. Generally, they have no other adverse effects on cellular metabolism, so that other glycosylation reactions proceed while the specific reaction is inhibited. The blocking agents are preferably relatively small molecules, thereby avoiding immunogenicity and allowing passage through the cell membrane. Ideally, they have a molecular weight of between about 100-2000 daltons, but may have molecular weights up to 5000 or more, depending upon the desired application. In most preferred embodiments, the inhibitors have molecular weights of between about 200-600 daltons.

The inhibitors of the present invention preferably have strong affinity for the target enzyme, so that at least about 70% inhibition of glycosyltransferase activity is achieved, more preferably about 75%-85% and most preferably 90%-95% or more. The affinity of the enzyme for the inhibitor is preferably sufficiently strong that the dissociation constant, or $K_i$, of the enzyme-inhibitor complex is less than about $10^{-5}$ M, typically between about $10^{-6}$ and $10^{-8}$ M.

Yet another tactic to inhibit glycosyltransferase activity is to use immunoglobulin molecules raised against the particular enzyme of interest. See, e.g., White et al., *Biochem.*, 29:2740-2747 (1990). Thus, the multitude of techniques available to those skilled in the art for production and manipulation of various immunoglobulin molecules can be applied to inhibit intercellular adhesion. The immunoglobulins may exist in a variety of forms besides antibodies, including for example, Fv, Fab, and F(ab)$_2$, as well as in single chains.

Antibodies which bind the enzyme may be produced by a variety of means. The production of non-human monoclonal antibodies, e.g., murine, lagomorpha, equine, etc., is well known and may be accomplished by, for example, immunizing the animal with glycosyltransferase or a fragment thereof conjugated to a carrier. Antibody-producing cells obtained from the immunized animals are immortalized and screened, or screened first for the production of antibody which inhibits the interaction of the enzyme with the substrate and then immortalized. For a discussion of general procedures of monoclonal antibody production, see, Harlow and Lane, *Antibodies, A Laboratory Manual* (1988).

Enzyme inhibition generally involves the interaction of a substance with an enzyme so as to decrease the rate of the reaction catalyzed by that enzyme. Inhibitors can be classified according a number of criteria. For example, they may be reversible or irreversible. An irreversible inhibitor dissociates very slowly, if at all, from its target enzyme because it becomes very tightly bound to the enzyme, either covalently or noncovalently. Reversible inhibition, in contrast, involves an enzyme-inhibitor complex which may dissociate.

Inhibitors can also be classified according to whether they are competitive, noncompetitive or uncompetitive inhibitors. In competitive inhibition for kinetically simple systems involving a single substrate, the enzyme can bind either the substrate or the inhibitor, but not both. Typically, competitive inhibitors resemble the substrate or the product(s) and bind the active site of the enzyme, thus blocking the substrate from binding the active site. A competitive inhibitor diminishes the rate of catalysis by effectively reducing the affinity of the substrate for the enzyme. Typically, an enzyme may be competitively inhibited by its own product because of equilibrium considerations. Since the enzyme is a catalyst, it is in principle capable of accelerating a reaction in the forward or reverse direction.

Noncompetitive inhibitors allow the enzyme to bind the substrate at the same time it binds the inhibitor. A noncompetitive inhibitor acts by decreasing the turnover number of an enzyme rather than diminishing the proportion of free enzyme. Another possible category of inhibition is mixed or uncompetitive inhibition, in which the inhibitor affects the binding site and also alters the turnover number of the enzyme. Enzyme inhibition of kinetically complex systems involving more than one substrate, as is the case for glycosyltransferases, are described in Segel, Enzyme Kinetics, (Wiley, N.Y. 1975).

C2 GlcNAc-T activity and its inhibition or enhancement is typically assayed according to standard methods for determining enzyme activity. For a general discussion of enzyme assays, see, Rossomando, "Measurement of Enzyme Activity" in *Guide to Protein Purification*, Vol. 182, Methods in Enzymology (Deutscher ed., 1990). An assay for C2 GlcNAc-T activity typically contains a buffered solution adjusted to physiological pH, a source of divalent cations, a donor substrate (usually labeled UDP-GlcNAc), an acceptor substrate (e.g., Galβ1,3GalNAc), the C2 GlcNAc-T, and the sample or fraction of a sample whose inhibitory activity is to be tested. After a predetermined time at 23° C. or 37° C., the reaction is stopped and the sialylated product is isolated and measured according to standard methods (e.g., in a scintillation counter).

B. Inhibition of Glycosyltransferase Gene Expression

Inhibition of glycosyltransferase gene expression can be achieved through the use of inhibitory nucleic acids. Inhibitory nucleic acids can be single-stranded nucleic acids that can specifically bind to a complementary nucleic acid sequence. By binding to the appropriate target sequence, an RNA-RNA, a DNA-DNA, or RNA-DNA duplex or triplex is formed. These nucleic acids are often termed "antisense" because they are usually complementary to the sense or coding strand of the gene, although recently approaches for use of "sense" nucleic acids have also been developed. The term "inhibitory nucleic acids" as used herein, refers to both "sense" and "antisense" nucleic acids.

In one embodiment, the inhibitory nucleic acid can specifically bind to a target nucleic acid that encodes an C2 GlcNAc-T. Administration of such inhibitory nucleic acids can inhibit B lymphocyte-mediated immune responses by reducing or eliminating the biosynthesis of core 2 oligosaccharides. Nucleotide sequences encoding C2 GlcNAc-T are known for several species, including the human cDNA (Bierhuizen and Fukuda (1992) *Proc. Nat'l. Acad. Sci. USA* 89: 9326-9330; GenBank Accession No. m97347). The human gene is described in Bierhuizen et al. (1995) *Glycobiol.* 5: 417-425; GenBank Accession No. L41415). From these nucleotide sequences, one can derive a suitable inhibitory nucleic acid.

By binding to the target nucleic acid, the inhibitory nucleic acid can inhibit the function of the target nucleic acid. This could, for example, be a result of blocking DNA transcription, processing or poly(A) addition to mRNA, DNA replication, translation, or promoting inhibitory mechanisms of the cells, such as promoting RNA degradation. Inhibitory nucleic acid methods therefore encompass a number of different approaches to altering expression of specific genes that operate by different mechanisms. These different types of inhibitory nucleic acid technology are described in Helene, C. and Toulme, J. (1990) *Biochim. Biophys. Acta.*, 1049:99-125.

Inhibitory nucleic acid therapy approaches can be classified into those that target DNA sequences, those that target RNA sequences (including pre-mRNA and mRNA), those that target proteins (sense strand approaches), and those that cause cleavage or chemical modification of the target nucleic acids.

Approaches targeting DNA fall into several categories. Nucleic acids can be designed to bind to the major groove of the duplex DNA to form a triple helical or "triplex" structure. Alternatively, inhibitory nucleic acids are designed to bind to regions of single stranded DNA resulting from the opening of the duplex DNA during replication or transcription. See Helene and Toulme, supra.

More commonly, inhibitory nucleic acids are designed to bind to mRNA or mRNA precursors. Inhibitory nucleic acids are used to prevent maturation of pre-mRNA. Inhibitory nucleic acids may be designed to interfere with RNA processing, splicing or translation. The inhibitory nucleic acids are often targeted to mRNA. In this approach, the inhibitory nucleic acids are designed to specifically block translation of the encoded protein. Using this approach, the inhibitory nucleic acid can be used to selectively suppress certain cellular functions by inhibition of translation of mRNA encoding critical proteins. For example, an inhibitory antisense nucleic acid complementary to regions of a target mRNA inhibits protein expression. See, e.g., Wickstrom E. L. et al. (1988) *Proc. Nat. 7. Acad. Sci. USA* 85:1028-1032 and Harel-Bellan et al. (1988) *Exp. Med.*, 168:2309-2318. As described in Helene and Toulme, inhibitory nucleic acids targeting mRNA have been shown to work by several different mechanisms in order to inhibit translation of the encoded protein(s).

The inhibitory nucleic acids introduced into the cell can also encompass the "sense" strand of the gene or mRNA to trap or compete for the enzymes or binding proteins involved in mRNA translation. See Helene and Toulme.

Lastly, the inhibitory nucleic acids can be used to induce chemical inactivation or cleavage of the target genes or mRNA. Chemical inactivation can occur by the induction of crosslinks between the inhibitory nucleic acid and the target nucleic acid within the cell. Alternatively, irreversible photochemical reactions can be induced in the target nucleic acid by means of a photoactive group attached to the inhibitory nucleic acid. Other chemical modifications of the target nucleic acids induced by appropriately derivatized inhibitory nucleic acids may also be used.

Cleavage, and therefore inactivation, of the target nucleic acids may be effected by attaching a substituent to the inhibitory nucleic acid which can be activated to induce cleavage reactions. The substituent can be one that effects either chemical, photochemical or enzymatic cleavage. For example, one can contact an mRNA:antisense oligonucleotide hybrid with a nuclease which digests mRNA:DNA hybrids. Alternatively cleavage can be induced by the use of ribozymes or catalytic RNA. In this approach, the inhibitory nucleic acids would comprise either naturally occurring RNA (ribozymes) or synthetic nucleic acids with catalytic activity.

In other embodiments, expression of glycosyltransferase genes is inhibited by administration of an agent that blocks the ability of a transactivating factor to induce gene expression. For example, one can administer an agent that interferes with the transactivating activity of tumor necrosis factor-alpha, interleukin-1, glucocorticoids (e.g., dexamethasone), retinoic acid, and some liver transcription factors (e.g., HNF-1, DBP and LAP).

The targeting of inhibitory nucleic acids to specific cells of the immune system by conjugation with targeting moieties binding receptors on the surface of these cells can be used for all of the above forms of inhibitory nucleic acid therapy.

C. Compounds that Block Core 2 Oligosaccharide-Mediated Binding

The invention also provides methods of modulating inflammation in which a compound is administered that blocks the interaction between a core 2 oligosaccharide and a ligand for the oligosaccharide. For example, one can administer an antibody or lectin that specifically binds to the core 2 oligosaccharide. Receptors that are not associated with an inflammatory cell (e.g., that are present as free polysaccharides) can be used to block the interaction between inflammatory cell-associated core 2 oligosaccharides and their cellular receptors. Other compounds, such as small molecules identified using the methods described herein, can also be administered.

II. Screening Methods

One can identify lead compounds that are suitable for further testing to identify those that are therapeutically effective modulating agents by screening a variety of compounds and mixtures of compounds for their ability to inhibit or enhance core 2 GlcNAcT activity, or which bind to a core 2 oligosaccharide and prevent the ligand from binding to its receptor. The testing can be performed using either a minimal core 2 oligosaccharide, or a modified core 2 oligosaccharide to which additional saccharide residues have been added. For example, one can test the ability of a lead compound to bind to a SLe$^x$-containing core 2 oligosaccharide.

The use of screening assays to discover naturally occurring compounds with desired activities is well known and has been widely used for many years. For instance, many compounds with antibiotic activity were originally identified using this approach. Examples of such compounds include monolactams and aminoglycoside antibiotics. Compounds which inhibit various enzyme activities have also been found by this technique, for example, mevinolin, lovastatin, and mevacor, which are inhibitors of hydroxymethylglutamyl Coenzyme A reductase, an enzyme involved in cholesterol synthesis. Antibiotics that inhibit glycosyltransferase activities, such as tunicamycin and streptovirudin have also been identified in this manner.

Thus, another important aspect of the present invention is directed to methods for screening samples for glycosyltransferase modulating activity. A "sample" as used herein may be any mixture of compounds suitable for testing in a glycosyltransferase assay. A typical sample comprises a mixture of synthetically produced compounds or alternatively a naturally occurring mixture, such as a cell culture broth. Suitable cells include any cultured cells such as mammalian, insect, microbial or plant cells. Microbial cell cultures are composed of any microscopic organism such as bacteria, protozoa, yeast, fungi and the like.

In the typical screening assay, a sample, such as a fungal broth, is added to a standard glycosyltransferase assay. If inhibition or enhancement of activity as compared to control assays is found, the mixture is usually fractionated to identify components of the sample providing the inhibiting or enhancing activity. The sample is fractionated using standard methods such as ion exchange chromatography, affinity chromatography, electrophoresis, ultrafiltration, HPLC and the like. See, e.g., *Protein Purification, Principles and Practice*, (Springer-Verlag, 1982). Each isolated fraction is then tested for or enhancing activity. If desired, the fractions are then further subfractionated and tested. This subfractionation and testing procedure can be repeated as many times as desired.

By combining various standard purification methods, a substantially pure compound suitable for in vivo therapeutic testing can be obtained. A substantially pure modulating agent as defined herein is an inhibitory or activity enhancing compound which migrates largely as a single band under standard electrophoretic conditions or largely as a single peak when monitored on a chromatographic column. More specifically, compositions of substantially pure modulating agents will comprise less than ten percent miscellaneous compounds.

In addition to assaying for an effect on C2 GlcNAc-T activity or core 2 oligosaccharide binding to identify suitable modulators of immune responses, one can test directly for an effect on inflammation. A standard assay for inflammation is the induction of peritonitis by injection of thioglycollate.

In preferred embodiments, the assays are designed to screen large chemical libraries by automating the assay steps and providing compounds from any convenient source to assays, which are typically run in parallel (e.g., in microtiter formats on microtiter plates in robotic assays).

As noted, the invention provides in vitro assays for Core 2 GlcNAcT activity in a high throughput format. For each of the assay formats described, "no modulator" control reactions which do not include a modulator provide a background level of Core 2 GlcNAcT activity. In the high throughput assays of the invention, it is possible to screen up to several thousand different modulators in a single day. In particular, each well of a microtiter plate can be used to run a separate assay against a selected potential modulator, or, if concentration or incubation time effects are to be observed, every 5-10 wells can test a single modulator. Thus, a single standard microtiter plate can assay about 100 (96) modulators. If 1536 well plates are used, then a single plate can easily assay from about 100- about 1500 different compounds. It is possible to assay many different plates per day; assay screens for up to about 6,000-20,000, and even up to about 100,000-1,000,000 different compounds is possible using the integrated systems of the invention.

In some assays it will be desirable to have positive controls to ensure that the components of the assays are working properly. For example, a known modulator of Core 2 GlcNAcT activity can be incubated with one sample of the assay, and the resulting increase or decrease in signal determined according to the methods herein.

Essentially any chemical compound can be tested as a potential modulator of C2 GlcNAc-T activity for use in the methods of the invention. Most preferred are generally compounds that can be dissolved in aqueous or organic (especially DMSO-based) solutions are used. It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs Switzerland) and the like.

In one preferred embodiment, modulators of C2 GlcNAcT activity or binding to core 2 oligosaccharides are identified by screening a combinatorial library containing a large number of potential therapeutic compounds (potential modulator compounds). Such "combinatorial chemical libraries" can be screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487-493 (1991) and Houghton et al., *Nature* 354:84-88 (1991)). Other chemistries for generating chemical diversity libraries can also be used. Such chemistries include, but are not limited to: peptoids (PCT Publication No. WO 91/19735), encoded peptides (PCT Publication WO 93/20242), random bio-oligomers (PCT Publication No. WO 92/00091), benzodiazepines (U.S. Pat. No. 5,288,514), diversomers such as hydantoins, benzodiazepines and dipeptides (Hobbs et al., *Proc. Nat. Acad. Sci. USA* 90:6909-6913 (1993)), vinylogous polypeptides (Hagihara et al., *J. Amer. Chem. Soc.* 114:6568 (1992)), nonpeptidal peptidomimetics with β-D-glucose scaffolding (Hirschmann et al., *J. Amer. Chem. Soc.* 114:9217-9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see, Ausubel, Berger and Sambrook, all supra), peptide nucleic acid libraries (see, e.g., U.S. Pat. No. 5,539,083), antibody libraries (see, e.g., Vaughn et al., *Nature Biotechnology*, 14(3):309-314 (1996) and PCT/US96/10287), carbohydrate libraries (see, e.g., Liang et al., *Science*, 274:1520-1522 (1996) and U.S. Pat. No. 5,593,853), small organic molecule libraries (see, e.g., benzodiazepines, Baum C&EN, Jan 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS, Advanced Chem. Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Asinex, Moscow, R", Tripos, Inc., St. Louis, Mo., ChemStar, Ltd, Moscow, RU, 3D Pharmaceuticals, Exton, Pa., Martek Biosciences, Columbia, Md., etc.).

III. Therapeutic and Diagnostic Uses of the Invention

The compositions and methods of the present invention can be used therapeutically to selectively inhibit or enhance glycosyltransferase activity (e.g., C2 GlcNAc-T) that is associated with a variety of conditions such as inflammation. The invention can be used to inhibit deleterious inflammatory responses such as, for example, acute inflammatory diseases and chronic inflammatory diseases. Representative examples of acute inflammatory disease include appendicitis, tonsillitis, delayed hypersensitivity reactions, inflammation due to sepsis, cutaneous inflammation and ischemic reperfusion injury. A representative example of a chronic inflammatory disease is rheumatoid arthritis.

In therapeutic applications, the glycosyltransferase inhibitors of the invention are administered to an individual already suffering from an inappropriate or undesirable immune response. Compositions that contain glycosyltransferase inhibitors or agents that bind to and block the core 2 glycans are administered to a patient in an amount sufficient to suppress the undesirable immune response and to cure or at least partially arrest symptoms and/or complications. An amount adequate to accomplish this is defined as "therapeutically effective dose." Amounts effective for this use will depend on, e.g., the inhibitor composition, the manner of administration, the stage and severity of the disease being treated, the weight and general state of health of the patient, and the judgment of the prescribing physician.

Alternatively, DNA or RNA that inhibits expression of one or more glycosyltransferase inhibitors, such as an antisense nucleic acid or a nucleic acid that encodes a peptide that blocks expression or activity of a glycosyltransferase can be introduced into patients to achieve inhibition. U.S. Pat. No. 5,580,859 describes the use of injection of naked nucleic acids into cells to obtain expression of the genes which the nucleic acids encode.

The invention also provides methods of treating conditions that are associated with a decrease in C2 GlcNAcT activity. For example, some types of cancer are characterized by the presence of T antigens, which are a series of O-glycans that are abbreviated due to the addition of a sialic acid residue by an ST3 Gal I or other sialyltransferase. The addition of the sialic acid to a nascent oligosaccharide prevents the synthesis of the normally present oligosaccharide structure. The invention provides methods of decreasing the frequency of these abnormally terminated T antigens by increasing the activity of C2 GlcNAcT activity in the patient. The increased C2 GlcNAcT activity can modify the acceptor substrates for the sialyltransferases, thus converting the putative acceptor into an oligosaccharide upon which the sialyltransferase cannot act.

Therapeutically effective amounts of the glycosyltransferase inhibitor or enhancer compositions of the present invention generally range for the initial administration (that is for therapeutic or prophylactic administration) from about 1.0 mg to about 10 g of glycosyltransferase inhibitor for a 70 kg patient, usually from about 10 mg to about 5 g, and preferably between about 2 mg and about 1 g. These doses can be followed by repeated administrations over weeks to months depending upon the patient's response and condition by measuring immune system activity.

It must be kept in mind that the compositions of the present invention may be employed in serious disease states, that is, life-threatening or potentially life threatening situations. In such cases, in view of the minimization of extraneous substances and the relative nontoxic nature of the inhibitors, it is possible and may be felt desirable by the treating physician to administer substantial excesses of these compositions.

For prophylactic use, administration should be given to risk groups. Therapeutic administration may begin at the first sign of disease or the detection or shortly after diagnosis in the case of immune disorder. This is often followed by repeated administration until at least symptoms are substantially abated and for a period thereafter.

The pharmaceutical compositions for therapeutic or prophylactic treatment are intended for parenteral, topical, oral or local administration. Typically, the pharmaceutical compositions are administered parenterally, e.g., intravenously, subcutaneously, intradermally, or intramuscularly. Compositions of the invention are also suitable for oral administration. Thus, the invention provides compositions for parenteral administration which comprise a solution of the glycosyltransferase inhibiting agent dissolved or suspended in an acceptable carrier, preferably an aqueous carrier. A variety of aqueous carriers may be used, e.g., water, buffered water, 0.9% saline, 0.3% glycine, hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

The concentration of glycosyltransferase inhibiting agents of the invention in the pharmaceutical formulations can vary widely, i.e., from less than about 0.1%, usually at or at least about 2% to as much as 20% to 50% or more by weight, and will be selected primarily by fluid volumes, viscosities, etc., in accordance with the particular mode of administration selected.

The glycosyltransferase inhibitors of the invention may also be administered via liposomes, which serve to target the conjugates to a particular tissue, such as lymphoid tissue, or targeted selectively to infected cells, as well as increase the half-life of the peptide composition. Liposomes include emulsions, foams, micelles, insoluble monolayers, liquid crystals, phospholipid dispersions, lamellar layers and the like. In these preparations the peptide to be delivered is incorporated as part of a liposome, alone or in conjunction with a molecule which binds to, e.g., a receptor prevalent among lymphoid cells, such as monoclonal antibodies which bind to the CD45 antigen, or with other therapeutic or immunogenic compositions. Thus, liposomes filled with a desired peptide or conjugate of the invention can be directed to the site of lymphoid cells, where the liposomes then deliver the selected glycosyltransferase inhibitor compositions. Liposomes for use in the invention are formed from standard vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety of methods are available for preparing liposomes, as described in, e.g., Szoka et al., *Ann. Rev. Biophys. Bioeng.* 9:467 (1980), U.S. Pat. Nos. 4,235,871, 4,501,728 and 4,837,028.

The targeting of liposomes using a variety of targeting agents is well known in the art (see, e.g., U.S. Pat. Nos. 4,957,773 and 4,603,044). For targeting to the immune cells, a ligand to be incorporated into the liposome can include, e.g., antibodies or fragments thereof specific for cell surface determinants of the desired immune system cells. A liposome suspension containing a peptide or conjugate may be administered intravenously, locally, topically, etc. in a dose which varies according to, inter alia, the manner of administration, the conjugate being delivered, and the stage of the disease being treated.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10-95% of active ingredient, that is, one or more conjugates of the invention, and more preferably at a concentration of 25%-75%.

For aerosol administration, the inhibitors are preferably supplied in a suitable form along with a surfactant and propellant. Typical percentages of glycosyltransferase inhibitors are 0.01%-20% by weight, preferably 1%-10%. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute 0.1%-20% by weight of the composition, preferably 0.25-5%. The balance of the composition is ordinarily propellant. A carrier can also be included, as desired, as with, e.g., lecithin for intranasal delivery.

The present invention also provides methods of monitoring inflammation by detecting the levels of core 2 glycans in a sample from a patient. This can be performed according to standard methods for detection of desired carbohydrate structures. Detection moieties that bind to, for example, the core 2 glycan, or to the acceptor substrate for the core 2 glycan, are used to detect whether the core 2 glycan is present in the sample.

In typical embodiments, the detection moieties are labeled with a detectable label. The detectable labels can be primary labels (where the label comprises an element that is detected directly or that produces a directly detectable element) or secondary labels (where the detected label binds to a primary label, as is common in immunological labeling). An introduction to labels, labeling procedures and detection of labels is found in Polak and Van Noorden (1997) *Introduction to Immunocytochemistry*, 2nd ed., Springer Verlag, NY and in Haugland (1996) *Handbook of Fluorescent Probes and Research Chemicals*, a combined handbook and catalogue published by Molecular Probes, Inc., Eugene, Oreg. Primary and secondary labels can include undetected elements as well as detected elements. Useful primary and secondary labels in the present invention can include spectral labels such as fluorescent dyes (e.g., fluorescein and derivatives such as fluorescein isothiocyanate (FITC) and Oregon Green™, rhodamine and derivatives (e.g., Texas red, tetrarhodimine isothiocyanate (TRITC), etc.), digoxigenin, biotin, phycoerythrin, AMCA, CyDyes™, and the like), radiolabels (e.g., $^3$H, $^{125}$I, $^{35}$S, $^{14}$C, $^{32}$P, $^{33}$P, etc.), enzymes (e.g., horse radish peroxidase, alkaline phosphatase etc.), spectral colorimetric labels such as colloidal gold or colored glass or plastic (e.g. polystyrene, polypropylene, latex, etc.) beads. The label may be coupled directly or indirectly to a component of the detection assay (e.g., the detection reagent) according to methods well known in the art. As indicated above, a wide variety of labels may be used, with the choice of label depending on sensitivity required, ease of conjugation with the compound, stability requirements, available instrumentation, and disposal provisions.

Preferred labels include those that use: 1) chemiluminescence (using horseradish peroxidase or luciferase) with substrates that produce photons as breakdown products as described above) with kits being available, e.g., from Molecular Probes, Amersham, Boehringer-Mannheim, and Life Technologies/Gibco BRL; 2) color production (using both horseradish peroxidase and/or alkaline phosphatase with substrates that produce a colored precipitate [kits available from Life Technologies/Gibco BRL, and Boehringer-Mannheim]); 3) hemifluorescence using, e.g., alkaline phosphatase and the substrate AttoPhos [Amersham] or other substrates that produce fluorescent products, 4) fluorescence (e.g., using Cy-5 [Amersham]), fluorescein, and other fluorescent tags]; 5) radioactivity. Other methods for labeling and detection will be readily apparent to one skilled in the art.

Preferred enzymes that can be conjugated to detection reagents of the invention include, e.g., luciferase, and horse radish peroxidase. The chemiluminescent substrate for luciferase is luciferin. Embodiments of alkaline phosphatase substrates include p-nitrophenyl phosphate (pNPP), which is detected with a spectrophotometer; 5-bromo-4-chloro-3-indolyl phosphate/nitro blue tetrazolium (BCIP/NBT) and fast red/napthol AS-TR phosphate, which are detected visually; and 4-methoxy-4-(3-phosphonophenyl) spiro[1,2-dioxetane-3,2'-adamantane], which is detected with a luminometer. Embodiments of horse radish peroxidase substrates include 2,2'-azino-bis(3-ethylbenzthiazoline-6 sulfonic acid) (ABTS), 5-aminosalicylic acid (SAS), o-dianisidine, and o-phenylenediamine (OPD), which are detected with a spectrophotometer; and 3,3,5,5'-tetramethylbenzidine (TMB), 3,3'-diaminobenzidine (DAB), 3-amino-9-ethylcarbazole (AEC), and 4-chloro-1-naphthol (4C1N), which are detected visually. Other suitable substrates are known to those skilled in the art.

In general, a detector which monitors a particular label is used to detect the label. Typical detectors include spectrophotometers, phototubes and photodiodes, microscopes, scintillation counters, cameras, film and the like, as well as combinations thereof. Examples of suitable detectors are widely available from a variety of commercial sources known to persons of skill. Commonly, an optical image of a substrate comprising bound labeling moieties is digitized for subsequent computer analysis.

Commercially available detection moieties that are suitable for use in the methods of the invention include SNA-fluorescein isothiocyanate (FITC) lectin (FL-1301, Vector Laboratories, Burlingame Calif.) and biotinylated SNA lectin (B-1305, Vector Laboratories) for $\alpha 2,3$ sialyl galactosides. For detection of $\alpha 2,6$ sialylgalactosides, MAL II-FITC lectin and biotinylated MAL II lectin (B-1265, Vector Laboratories) are examples of suitable detection moieties.

An effective anti-inflammatory treatment is indicated by a decrease in the presence of core 2 glycans in a sample, e.g., neutrophils, obtained from the patient. Alternatively, methods for detecting levels of specific glycosyltransferase activities can be used. Standard assays for detecting glycosyltransferases such as the C2 GlcNAc-T are described herein. Again, an effective anti-inflammatory treatment is indicated by a substantial reduction in activity of the particular glycosyltransferase. As used herein, a "substantial reduction" in the appropriate core 2 glycan levels or glycosyltransferase activity refers to a reduction of at least about 30% in the test sample compared to an untreated control. Preferably, the reduction will be at least about 50%, more preferably at least about 75%, and most preferably core 2 glycan or C2 GlcNAc-T levels will be reduced by at least about 90% in a sample from a treated mammal compared to an untreated control.

IV. Transgenic Animals that Lack C2 GlcNAc-T

The invention also provides chimeric and transgenic nonhuman animals which contain cells that lack at least one C2 GlcNAc-T gene that is found in wild-type cells of the animal, and methods for producing such animals. These animals are useful for several purposes, including the study of the mechanisms by which core 2 oligosaccharides influence inflammatory and other effects. Such "knockout" animals can also be used for producing glycoproteins and glycolipids that, when produced in a wild-type animal, would carry a sialic acid residue that is not desirable for a particular application.

A "chimeric animal" includes some cells that lack the functional C2 GlcNAc-T gene and other cells that do not have the inactivated gene. A "transgenic animal," in contrast, is made up of cells that have all incorporated the specific modification which renders the C2 GlcNAc-T gene inactive. While a transgenic animal is capable of transmitting the inactivated C2 GlcNAc-T gene to its progeny, the ability of a chimeric animal to transmit the mutation depends upon whether the inactivated gene is present in the animal's germ cells. The modifications that inactivate the C2 GlcNAc-T gene can include, for example, insertions, deletions, or substitutions of one or more nucleotides. The modifications can interfere with transcription of the gene itself, with translation and/or stability of the resulting mRNA, or can cause the gene to encode an inactive C2 GlcNAc-T polypeptide.

The claimed methods are useful for producing transgenic and chimeric animals of most vertebrate species. Such species include, but are not limited to, nonhuman mammals, including rodents such as mice and rats, rabbits, ovines such as sheep and goats, porcines such as pigs, and bovines such as cattle and buffalo. Methods of obtaining transgenic animals are described in, for example, Puhler, A., Ed., *Genetic Engineering of Animals*, VCH Publ., 1993; Murphy and Carter, Eds., *Transgenesis Techniques: Principles and Protocols* (*Methods in Molecular Biology*, Vol. 18), 1993; and Pinkert, C A, Ed., *Transgenic Animal Technology: A Laboratory Handbook*, Academic Press, 1994.

One method of obtaining a transgenic or chimeric animal having an inactivated C2 GlcNAc-T gene in its genome is to contact fertilized oocytes with a vector that includes a C2 GlcNAc-T-encoding polynucleotide that is modified to contain an inactivating modification. For some animals, such as mice, fertilization is performed in vivo and fertilized ova are surgically removed. In other animals, particularly bovines, it is preferably to remove ova from live or slaughterhouse animals and fertilize the ova in vitro. See DeBoer et al., WO 91/08216. In vitro fertilization permits the modifications to be introduced into substantially synchronous cells. Fertilized oocytes are then cultured in vitro until a pre-implantation embryo is obtained containing about 16-150 cells. The 16-32 cell stage of an embryo is described as a morula. Pre-implantation embryos containing more than 32 cells are termed blastocysts. These embryos show the development of a blastocoel cavity, typically at the 64 cell stage. If desired, the presence of a desired inactivated C2 GlcNAc-T gene in the embryo cells can be detected by methods known to those of skill in the art. Methods for culturing fertilized oocytes to the pre-implantation stage are described by Gordon et al. (1984) *Methods Enzymol.* 101: 414; Hogan et al. *Manipulation of the Mouse Embryo: A Laboratory Manual*, C. S. H.

L. N. Y. (1986) (mouse embryo); Hammer et al. (1985) *Nature* 315: 680 (rabbit and porcine embryos); Gandolfi et al. (1987) *J. Reprod. Fert.* 81: 23-28; Rexroad et al. (1988) *J Anim. Sci.* 66: 947-953 (ovine embryos) and Eyestone et al. (1989) *J. Reprod. Fert.* 85: 715-720; Camousetal. (1984) *J. Reprod. Fert.* 72: 779-785; and Heyman et al. (1987) *Theriogenology* 27: 5968 (bovine embryos). Sometimes pre-implantation embryos are stored frozen for a period pending implantation. Pre-implantation embryos are transferred to an appropriate female resulting in the birth of a transgenic or chimeric animal depending upon the stage of development when the transgene is integrated. Chimeric mammals can be bred to form true germline transgenic animals.

Alternatively, the modified C2 GlcNAc-T gene can be introduced into embryonic stem cells (ES). These cells are obtained from preimplantation embryos cultured in vitro. See, e.g., Hooper, M L, *Embryonal Stem Cells: Introducing Planned Changes into the Animal Germline* (Modern Genetics, v. 1), Int'l. Pub. Distrib., Inc., 1993; Bradley et al. (1984) *Nature* 309, 255-258. Transformed ES cells are combined with blastocysts from a nonhuman animal. The ES cells colonize the embryo and in some embryos form the germ line of the resulting chimeric animal. See, Jaenisch (1988) *Science* 240: 1468-1474. Alternatively, ES cells or somatic cells that can reconstitute an organism ("somatic repopulating cells") can be used as a source of nuclei for transplantation into an enucleated fertilized oocyte giving rise to a transgenic mammal. See, e.g., Wilmut et al. (1997) *Nature* 385: 810-813.

The introduction of the modified C2 GlcNAc-T gene into recipient cells can be accomplished by methods known to those of skill in the art. For example, the modified gene can be targeted to the wild type sialyltransferase locus by homologous recombination. Alternatively, a recombinase system can be employed to delete all or a portion of a locus of interest. Examples of recombinase systems include, the cre/lox system of bacteriophage P1 (see, e.g., Gu et al. (1994) *Science* 265: 103-106; Terry et al. (1997) *Transgenic Res.* 6: 349-356) and the FLP/FRT site specific integration system (see, e.g., Dymecki (1996) *Proc. Nat'l. Acad. Sci. USA* 93: 6191-6196). In these systems, sites recognized by the particular recombinase are typically introduced into the genome at a position flanking the portion of the gene that is to be deleted. Introduction of the recombinase into the cells then catalyzes recombination which deletes from the genome the polynucleotide sequence that is flanked by the recombination sites. If desired, one can obtain animals in which only certain cell types lack the sialyltransferase gene of interest. See, e.g., Tsien et al. (1996) *Cell* 87: 1317-26; Brocard et al. (1996) *Proc. Nat'l. Acad. Sci. USA* 93: 10887-10890; Wang et al. (1996) *Proc. Nat'l. Acad. Sci. USA* 93: 3932-6; Meyers et al. (1998) *Nat. Genet.* 18: 136-41).

EXAMPLES

The following examples are offered to illustrate, but not to limit the present invention.

Example 1

Mammalian serine/threonine-linked oligosaccharides (O-glycans) are commonly synthesized with the Golgi enzyme core 2 β-1,6-N-acetylglucosaminyltransferase (C2 GlcNAcT). Core 2 O-glycans have been hypothesized to be essential for mucin production and selectin ligand biosynthesis. This Example demonstrates that mice lacking C2 GlcNAcT exhibit a restricted phenotype with neutrophilia and a partial deficiency of selectin ligands. Loss of core 2 oligosaccharides reduces neutrophil rolling on substrata bearing E-, L- and P-selectins and neutrophil recruitment to sites of inflammation. However, the diminished presence of L-selectin ligands on lymph node high endothelial venules does not affect lymphocyte homing. These studies indicate that core 2 oligosaccharide biosynthesis segregates the physiologic roles of selectins and reveal a function for the C2 GlcNAcT in myeloid homeostasis and inflammation.

Experimental Procedures

Iisolation of mouse C2 GlcNAcT genomic DNA and construction of a targeting vector bearing Cre loxP recombination signals was accomplished similarly as described (Priatel et al. (1997) *Glycobiology* 7: 45-56). R1 ES cells (Nagy et al. (1993) *Proc. Nat'l Acad. Sci. USA* 90: 8424-8428) were electroporated with 10 μg of the linearized targeting construct and the resulting clones were screened by Southern blotting using the genomic probe. Targeted ES cells were electroporated with 5 μg of Cre expression plasmid and subclones bearing the C2 GlcNAcT$^\Delta$ and C2 GlcNAcT$_F$ alleles were isolated. C2 GlcNAcT$^\Delta$ and C2 GlcNAcT$^F$ chimeric mice were generated using standard techniques (Metzler et al. (1994) *EMBO J.* 13: 2056-2065) and were crossed into the C57BL/6 background for the generation of heterozygous offspring. C2 GlcNAcT allelic structure was analyzed by Southern blotting and PCR. The wild type C2 GlcNAcT allele was detected using PCR primers adjacent to the deleted region (W5': 5'-GGG TTA CGG ATG AGCTCT GTG TC-3' (SEQ ID NO:1) and W3':5'-CCC TGG AAG CAG GAC AAT TCT G-3' (SEQ ID NO:2)) resulting in a 304 bp fragment, while the mutant allele was detected using W5' and a loxP primer (M3':5'-CTC GAA TTG ATC CCC GGG TAC-3' (SEQ ID NO:3)) yielding a 200 bp fragment.

B. C2 GlcNAcT Enzyme Assays and Oligosaccharide Analysis

The enzyme assay mixture containing 50 mM Mes (pH 7.0), 0.5 μCi of UDP-[$^3$H]GlcNAc in 1 mM UDP-GlcNAc, 0.1 M GlcNAc, 10 mM EDTA, 1 mM acceptor and 25 μl cell lysate from normal, heterozygous or homozygous null tissues in a total volume of 50 μl was incubated at 37° C. for 1 h followed by C18 Sep-Pak (Waters) processing (Bierhuizen and Fukuda (1992) *Proc. Nat'l. Acad. Sci. USA* 89: 9326-9330; Yousefi et al. (1991) *J. Biol. Chem.* 266: 1772-1782). For oligosaccharide analyses, splenocytes from wild type or C2 GlcNAcT null animals were metabolically labeled with [$^3$H]glucosamine (10 μCi/ml) for 24 h and processed according to described procedures (Bierhuizen et al. (1994) *J. Biol. Chem.* 269: 4473-4479; Maemura and Fukuda (1992) *J. Biol. Chem.* 267: 24379-24386). O-Linked oligosaccharides were initially analyzed by Bio-Gel P-4 gel filtration as previously reported (Maemura and Fukuda (1992), supra.). Sialylated O-glycans were then desialylated and analyzed by HPLC using an amino-bonded column and standard techniques (Piller et al. (1988) *J. Exp. Med.* 173: 1501-1510.

C. Flow Cytometry

Single cell suspensions of splenocytes were prepared and erythrocytes removed by ammonium chloride lysis. Cells were incubated in the presence of antibodies (below) in FACS buffer (2% FCS in PBS) for 20 minutes at 4° C. For E- or P-selectin binding, cells were treated with 0.5 μg/ml of Fc Block (anti-CD32/16, PharMingen), then incubated with Gr-1 and either the E- or P-selectin-IgM chimera (Maly et al.

(1996) *Cell* 86: 643-653) with or without addition of 5 mm EDTA for 30 minutes at 4° C. Cells were washed and incubated with a goat anti-human FITC conjugated secondary antibody (Sigma) as appropriate. Antibodies used were CD11a (M17/4), CD11b (M1/70), CD18 (C71/16), CD22 (Cy34.1), CD24 (M1/69), CD43 (S7 and 1B11), CD45 (30-F11), CD45R/B220 (RA3-6B2), CD62L (MEL-14), and Gr-1 (RB6-8C5) (PharMingen). The anti-PSGL-1 antibody, 4RA10 was a generous gift from Dr. D. Vestweber. Data were analyzed on a FACScan flow cytometer using CELLQUEST™ software (Becton Dickinson).

D. Hematology

Blood from the tail vein of methoxyfluorane anethetized mice was collected into EDTA-coated polypropylene microtubes (Becton Dickinson). Analyses of red blood cells, white blood cells and platelet cell numbers and morphology were carried out manually and with a CELL-DYN 3500 calibrated with normal mouse blood (UCSD Medical Center, Hillcrest).

E. Bone Marrow Progenitor Assay

Bone marrow was flushed from the femurs of wild type or C2 GlcNAcT null mice with 2% FBS in PBS and single cell suspensions prepared by aspirating gently through a 25 g needle. $1.5 \times 10^4$ nucleated cells were plated into 35 mm dishes in triplicate in Methocult M3434 (Stemcell Technologies Inc.). Dishes were incubated at 37° C., 5% $CO_2$ for 10-12 days and colonies enumerated using light microscopy.

F. Leukocyte Rolling

Soluble murine E-, P- and L-selectin IgG chimeric molecules were coated onto polystyrene dishes and assembled in a parallel plate flow chamber (GlycoTech, Rockville, Md.). Neutrophils from wild type, C2 GlcNAcT$^{\Delta/\Delta}$ or FucT-VII$^{-/-}$ mice were prepared at a concentration of $1 \times 10^6$/ml in rolling medium, 0.2% BSA in HBSS without calcium and magnesium (Life Technologies, Inc., Gaithersburg, Md.) supplemented with 10 mM HEPES, pH 7.2. The calcium concentration was adjusted to 2 mM immediately prior to infusion of the neutrophils into the flow chamber for 30 seconds at 5 dyn/cm² using a syringe pump (KD Scientific Inc., Boston, Mass.). This infusion was stopped for 3 min to allow for static adhesion of the neutrophils to the substrate and then restarted at 0.19 dyn/cm². Wall shear forces were doubled every two minutes without interrupting the cell flow. Fields of neutrophils were observed using a 10× objective, and the scene was recorded on VCR tape. Image analysis was performed on 6100/66 Power Macintosh using the Scion version of the public domain NIH Image program (Scion Corporation, Frederick, Md.). The fraction of cells remaining adherent under static conditions after 2 minutes at each specific shear force was determined by manually enumerating the cells and dividing this number by the number of adherent cells observed immediately preceding the initiation of flow (i.e., 100% represents cells found in the observed field after static adhesion, prior to initiation of the lowest shear flow rate).

G. Peritoneal Inflammation

Mice were injected intraperitoneally with 1 ml of 3% thioglycollate (Sigma). At the indicated times, mice were sacrificed and the peritoneal cavities lavaged with 10 ml of ice cold PBS containing 1% BSA and 0.5 mM EDTA. Red blood cells were removed by hypotonic lysis and leukocytes counted manually using a hemocytometer. Cytospins were stained with Leukostat (Sigma) and neutrophils counted. Peritoneal exudates were also stained with Gr-1 and F4/80 (Caltag) and analyzed by flow cytometry.

H. Lymphocyte Trafficking

To determine the cellularity of secondary lymphoid organs, tissues were dissected from wild type and C2 GlcNAcT homozygous null mice. Single cell suspensions of lymphocytes from mesenteric lymph nodes, peripheral (axillary and brachial) lymph nodes and Peyer's patches were enumerated manually using a hemocytometer. Frozen sections of axillary and brachial lymph nodes were cut at 5 μm, air dried and fixed in acetone prior to staining with hematoxylin and eosin. In separate experiments, an L-selectin-IgM was applied to frozen sections of peripheral lymph nodes as previously described (Maly et al. (1996) supra.; Smith et al. (1996) *J. Biol. Chem.* 271: 8250-8259). Serial sections were stained with the peripheral node addressin antibody, MECA 79. Lymphocyte homing assays were carried out as previously described (Maly et al. (1996), supra. Briefly, $2.5 \times 10^7$ CMFDA (Molecular Bioprobes) labeled wild type mesenteric leukocytes were injected into the tail vein of wild type or C2 GlcNAcT$^{\Delta/\Delta}$ mice. After 1 h, the animals were sacrificed and hematopoietic organs removed. Analysis of 100,000 CMFDA positive leukocytes was carried out by flow cytometry.

L Statistical Analysis

Data were analyzed by Student's t test for unpaired samples using StatView® software.

Results

A. Targeted Mutagenesis and Deletion of the C2 GlcNAcT Gene

Figure 2:
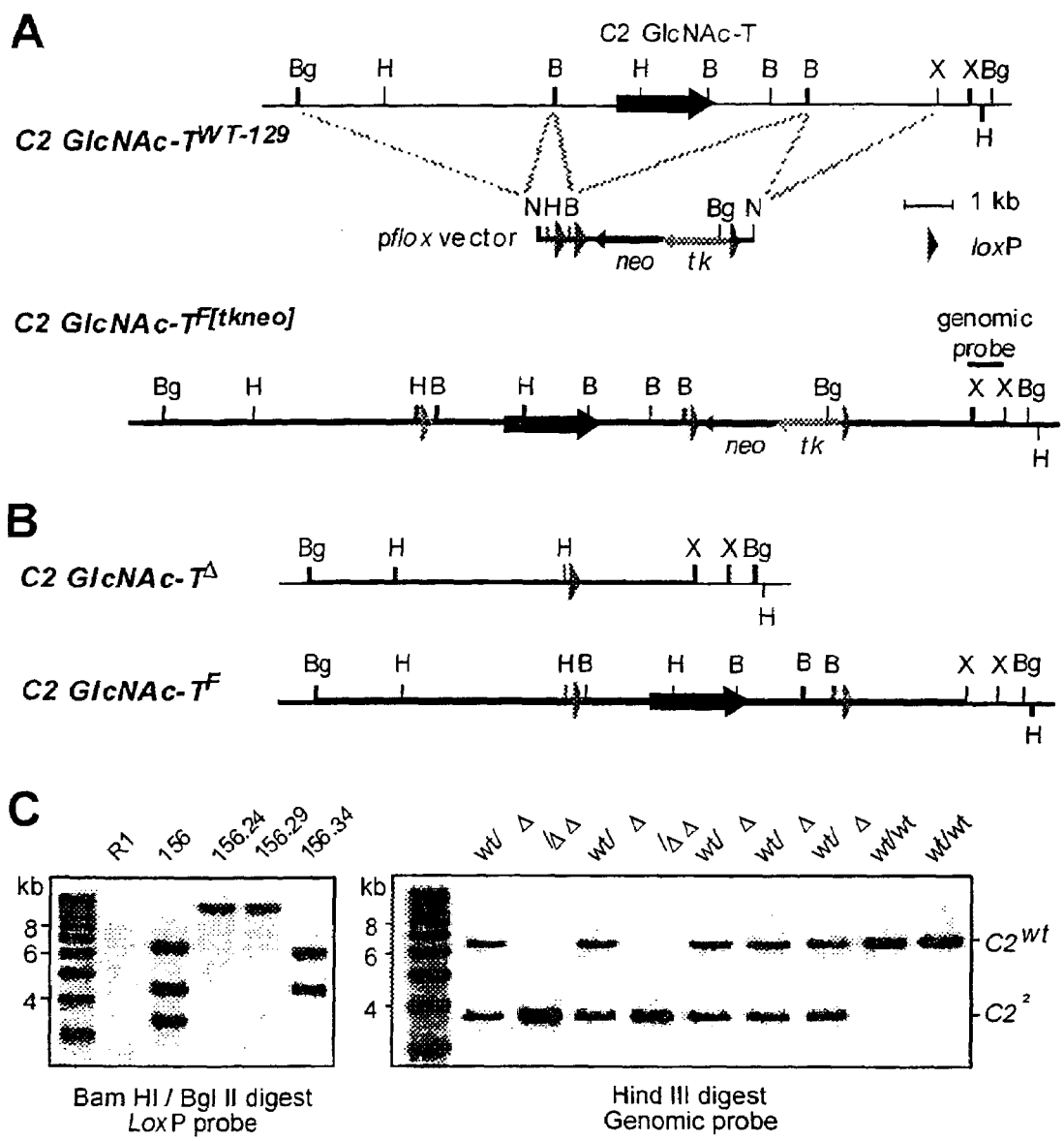
FIGS. 2A-2C show the strategy used for deletion of the C2GlcNAcT gene in embryonic stem cells and mice.

C2 GlcNAcT is a Golgi localized type II transmembrane glycosyltransferase and is conserved among mammals studied (Bierhuizen and Fukuda (1992) *J. Biol. Chem.* 89: 9326-9330; Sekine et al. (1997) *J. Biol. Chem.* 272: 27246-27252). A mouse genomic clone encompassing the single C2 GlcNAcT protein-coding exon was used in constructing a gene-targeting vector designed to control exon deletion by Cre- loxP recombination (FIG. 2A). Homologous recombination of the targeting vector in embryonic stem (ES) cells incorporated selection markers and 3 loxP sites for the subsequent production of systemic C2 GlcNAcT$^{\Delta}$ or conditional C2 GlcNAcT$^F$ mutations in vivo (FIG. 2B and FIG. 2C). These alleles were transmitted into the mouse germline and offspring homozygous for either the C2 GlcNAcT$^{\Delta}$ or C2 GlcNAcT$^F$ allele were generated. Such offspring were present among 25% of littermates, lacked overt physical or behavioral abnormalities, developed normally and were fully fertile. Mice homozygous for C2 GlcNAcT$^{\Delta}$ allele were further analyzed.

B. C2 GlcNAcT Activity and Core 2 O-Glycan Abundance

Figure 3:
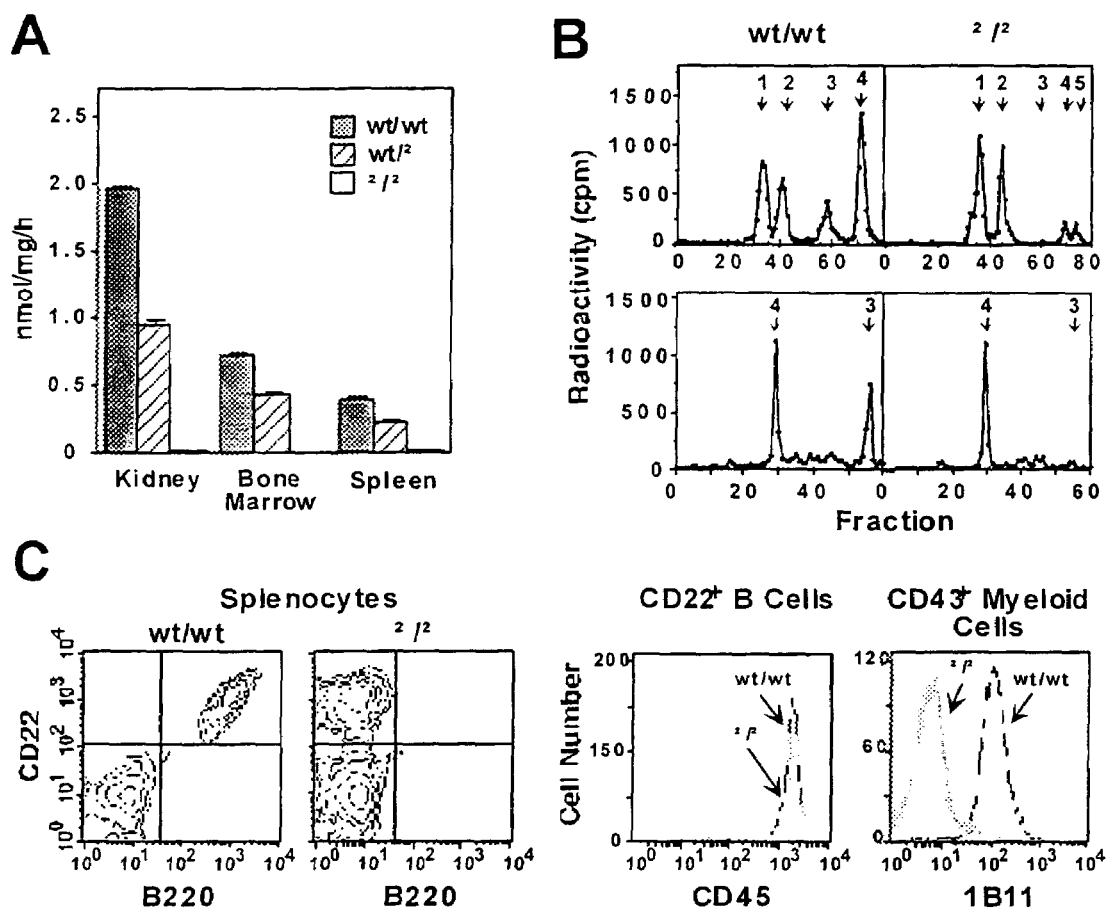
FIGS. 3A-3C demonstrate C2GlcNAcT activity and oligosaccharide production.

C2 GlcNAcT enzyme activity is specifically detected by using a substrate analogue of the core 1 oligosaccharide (Yousefi et al. (1991) *J. Biol. Chem.* 266: 1772-1782). In mice homozygous for the C2 GlcNAcT$^{\Delta}$ allele, tissues normally expressing high C2 GlcNAcT levels were devoid of significant activity, including the spleen, bone marrow and kidney (FIG. 3A). To determine whether loss of C2 GlcNAcT activity resulted in a deficiency of core 2 O-glycans, oligosaccharide structures were analyzed in metabolically-labeled splenocytes. O-linked oligosaccharides isolated from splenocytes homozygous for the C2 GlcNAcT$^{\Delta}$ allele lacked Galβ1-3(Galβ1-4GlcNAcβ1-6)GalNAc, indicating a deficiency of core 2 O-glycans (FIG. 3B upper panel, peak 3). Desialylation and additional chromatographic analysis further indicated a loss of core 2 O-glycans (FIG. 3B lower panel, peak 3). The majority of core 1 oligosaccharides in C2 GlcNAcT deficient splenocytes were sialylated, consistent with structures expected in the absence of C2 GlcNAcT activity.

Monoclonal antibodies previously implicated as oligosaccharide-dependent were also applied to characterize C2 GlcNAcT deficient cells. B lymphocytes specifically express CD22 and the B cell epitope B220 the latter of which is a glycoform of CD45 (Johnson et al. (1989) *J. Exp. Med.* 169: 1179-84). Splenocytes lacking C2 GlcNAcT activity were devoid of the B220 epitope, while CD22 and CD45 protein levels at the cell surface were unaltered (FIG. 3C, left panels). The CD43 glycoprotein is highly expressed on leukocytes as two distinct glycoforms differentially recognized by monoclonal antibodies S7 and 1B11. The high molecular weight CD43 glycoform expressed on myeloid cells is modified with core 2 O-linked oligosaccharides and is recognized by the 1B11 antibody (Jones et al. (1994) *J. Immunol.* 153: 3426-3439). In mice homozygous for the C2 GlcNAcT$^\Delta$ allele, myeloid cells remained positive for S7 binding, while 1B11 antibody binding was distinctly absent (FIG. 3C, right panels). These data reveal that homozygosity at the C2 GlcNAcT$^\Delta$ allele results in a deficiency of C2 GlcNAcT activity and core 2 O-glycans.

C. C2 GlcNAcT Deficiency Results in a Moderate Neutrophilia

Figure 4:
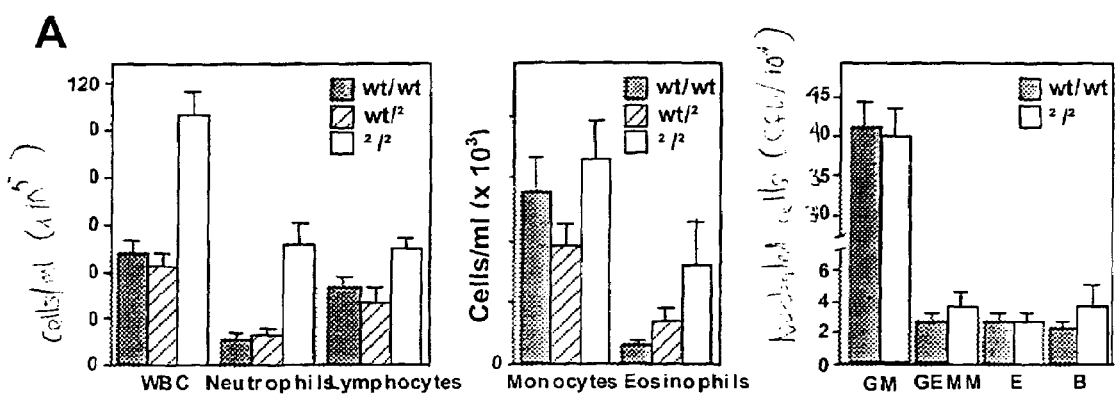
FIGS. 4A and 4B show the peripheral hematology in C2 GlcNAcT deficient mice. Blood was collected from the tail vein of 6-8 week old mice. Automated total white blood cell counts and automated and manual differential counts were carried out using a CELL-DYN 3500 and Wright-Giemsa stained smears. Counts from 20 mice of each genotype are expressed as cells per ml of whole blood ±SEM.
FIG. 4C shows colony forming units in the bone marrow, which were analyzed by in vitro differentiation of nucleated bone marrow cells in methylcellulose in the presence of growth factors. The number of colony-forming units (GM—granulocyte/macrophage; GEMM—granulocyte/erythroblast/macrophage/monocyte; E—erythroblast; B-B cell) was counted at day 10. Data are means ±SEM from 6 mice of each genotype.

Upon histologic examination, no alterations were detected in cellular or organ morphologies within C2 GlcNAcT deficient mice. The kidney, lungs, the intestinal tract, and associated epithelium were unremarkable and mucin levels in the intestinal goblet cells were indistinguishable from controls (data not shown). Analyses of serum biochemistry indicated normal renal function (data not shown). Hematologic examination disclosed a blood leukocytosis. Total white blood cell counts were elevated 2.4 fold in C2 GlcNAcT null mice. This increase was almost entirely accounted for by a 4.3 fold increase in neutrophils (FIG. 4A). Bone marrow progenitor cell numbers were normal in C2 GlcNAcT null mice, implying that the leukocytosis is not a consequence of increased neutrophil production (FIG. 4B). In other studies, circulating platelet levels and morphology were also unchanged and no difference in bleeding time was apparent (data not shown). These observations are reminiscent of certain results obtained from mice deficient in selectins or selectin ligands.

D. C.2 GlcNAcT Participates in Selectin Ligand Formation and Leukocyte Rolling

Figure 5:
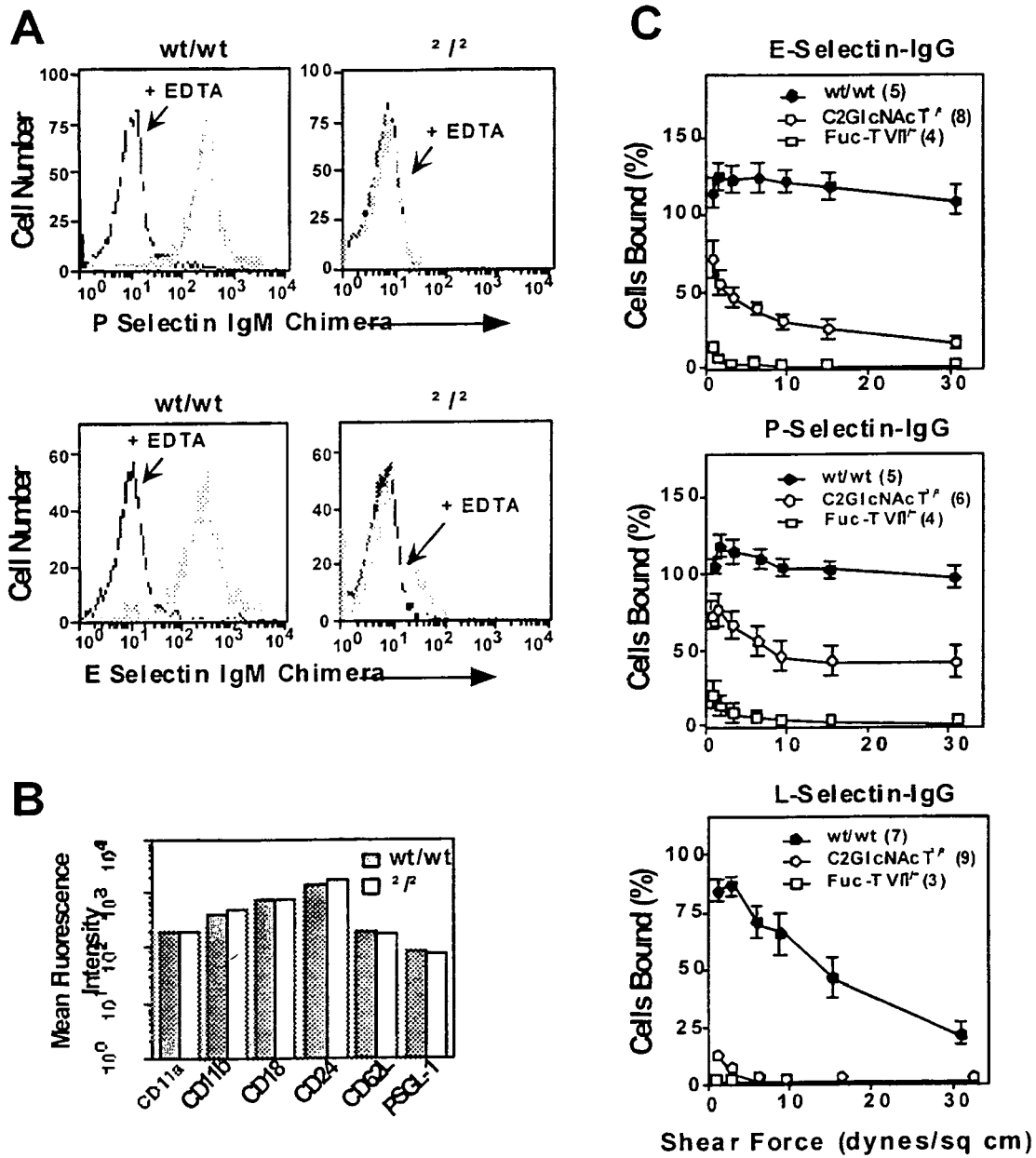
FIGS. 5A-5B show leukocyte selectin ligand expression.
FIG. 5C shows results from an experiment in which peripheral blood neutrophils from wild type, C2 GlcNAcT null and FucT-VII null mice were infused into a flow chamber coated with immobilized E-, P- or L-selectin IgG chimeras. Static adhesion of cells was recorded after stopping the flow for 3 minutes and rolling counts were recorded on video after application of specific shear forces. The number of independent measurements is indicated in parentheses. Data represent the mean ±SEM. Site densities were as follows: E-selectin-IgG, 63 molecules per square micrometer; L-selectin IgG, 2,840 molecules per square micrometer; P-selectin-IgG, 1,469 molecules per square micrometer.

To detect a role for C2 GlcNAcT in selectin ligand biosynthesis, selectin-Ig chimeras were used to examine levels of E-, L- and P-selectin ligands on cell surfaces. The E- and P-selectin chimeras specifically bind to carbohydrate ligands on myeloid cells in the blood including granulocytes and monocytes (Maly et al. (1996) *Cell* 86: 643-653). Using flow cytometry, peripheral blood leukocytes from C2 GlcNAcT null mice were found to be deficient in both E- and P-selectin ligands. The P-selectin chimera did not significantly bind whereas a low level of E-selectin-Ig binding remained (FIG. 5A). These results were not due to reduced expression of proteins that carry selectin ligands. Cell surface levels of PSGL-1, L-selectin and CD24 on C2 GlcNAcT deficient leukocytes were unaffected, as were levels of various adhesion molecules involved in the firm attachment of leukocytes to the endothelium (CD11a, CD11b and CD18; FIG. 5B).

Figure 6:
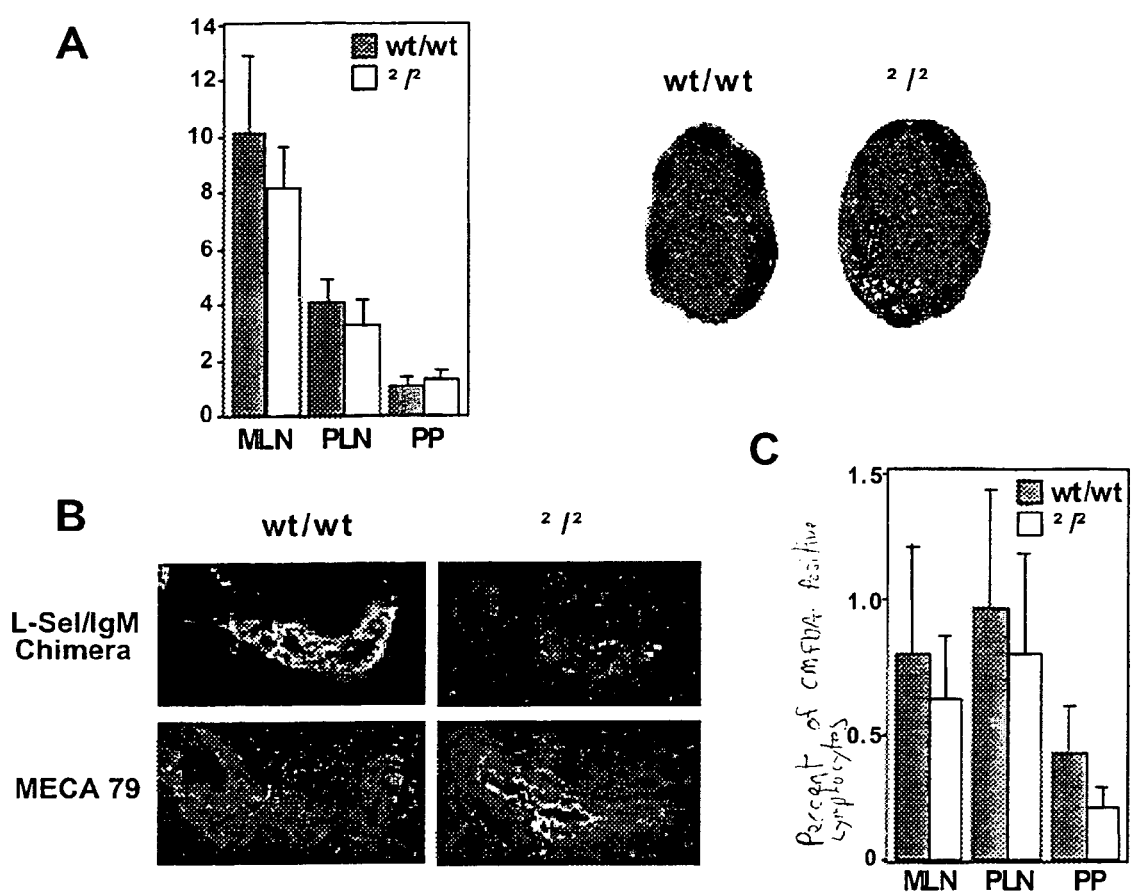
FIGS. 6A-6C show results of an analysis of lymph node morphology, L-selectin binding and lymphocyte homing.

A parallel plate flow chamber system was used to measure the contribution of core 2 oligosaccharides to functional selectin binding. Immobilized E-, L- or P-selectin-Ig chimeras served as the adhesion substrate for neutrophil rolling in this system. The binding of FucT-VII null leukocytes was monitored in direct comparisons as they do not appreciably bind selectins at most shear forces (Maly et al., supra.). Leukocytes deficient in core 2 oligosaccharides exhibited reduced but significant rolling activity on E- and P-selectins at all shear forces used, while FucT-VII null leukocytes did not interact appreciably with the immobilized selectin-Ig chimeras (FIG. 6). At the highest shear forces, 50% of C2 GlcNAcT null leukocytes remained bound to the P-selectin substrate and approximately 20% bound to the E-selectin substrate. In contrast, leukocyte rolling on L-selectin appeared especially dependent upon core 2 oligosaccharide biosynthesis as C2 GlcNAcT deficient leukocytes were unable to bind except at shear forces below 10 dynes/cm$^2$.

E. Core 2 Oligosaccharides Recruit Neutrophils to Sites of Inflammation

Since core 2 oligosaccharides contribute to selectin ligand biosynthesis, it seemed likely that C2 GlcNAcT null mice would exhibit abnormalities in lymphocyte trafficking and neutrophil recruitment to sites of inflammation. During the first four hours following an inflammatory stimulus, neutrophil recruitment to sites of inflammation is largely dependent upon selectin function (Mayadas et al. (1993) *Cell* 74: 541-554). Peritonitis induced by thioglycollate injection can be used to assess selectin function in a model of acute inflammation involving quantitation of neutrophil recruitment in vivo. In the absence of core 2 oligosaccharides, a severe deficit in neutrophil recruitment to inflamed peritoneum was apparent with only 20% of control neutrophil numbers recoverable at 4 hours (Table 1). This extent of reduction in neutrophil numbers is similar in FucT-VII deficient mice which are more deficient in selectin ligand formation (Maly et al., supra.). These data indicate that core 2 oligosaccharides provide an essential function in selectin-mediated neutrophil recruitment during acute inflammation.

TABLE I

Neutrophil Recruitment to Peritoneal Exudates during Inflammation

| Hours Post-Stimulus | C2 GlcNAcT$^{wt/wt}$ | C2 GlcNAcT$^{\Delta/\Delta}$ |
|---|---|---|
| 0 | 4 ± 1 (n = 3) | 4 ± 1 (n = 3) |
| 2 | 48 ± 6 (n = 10) | 5 ± 1 (n = 7)* |
| 4 | 499 ± 86 (n = 10) | 96 ± 19 (n = 12)* |

Data are the means ± SEM of neutrophil numbers (× 10$^4$) recovered from the peritoneal lavage of thioglycollate-treated mice. The number of mice in each group is indicated in parentheses. An unpaired t test indicated significance of *p < 0.001.

F. L-Selectin Ligands Produced by C2 GlcNAcT are Dispensable for Lymphocyte Homing L-selectin and FucT-VII are crucial for lymphocyte homing to the lymph nodes (Arbones et al. (1994) *Immunity* 1: 247-260; Maly et al., supra.). Since L-selectin counter-receptors on HEVs may be sialylated mucins, it seemed likely that C2 GlcNAcT was involved in their production. However, secondary lymphoid organs from C2 GlcNAcT deficient mice exhibited normal tissue size and follicular anatomy without alterations in either lymphocyte abundance or subset proportions (FIG. 6A). Nevertheless, L-selectin binding to lymph node HEVs was reduced in the absence of C2 GlcNAcT (FIG. 6B). This deficit in L-selectin ligand formation was not apparent using higher concentrations of the L-selectin-Ig chimera (data not shown) and was without significant consequence as lymphocyte homing to C2 GlcNAcT deficient lymph nodes and spleen was statistically unaltered (FIG. 6C and data not shown). These results indicate that C2 GlcNAcT activity in HEV L-selectin biosynthesis is dispensable for lymphocyte homing to secondary lymphoid organs.

Discussion

The C2 GlcNAcT glycosyltransferase is essential for the biosynthesis of core 2 O-glycans in leukocytes. Loss of C2 GlcNAcT provides a unique model of selectin ligand deficiency that results in a deficit in the inflammatory response while lymphocyte homing remains intact. Defining the structural basis of physiologic selectin ligands is of continued relevance as this study reveals that selectin ligand biosynthesis and function are differentially regulated among various anatomic compartments. Some glycosyltransferases and glycosidases have been found to function with a significant degree of cell-type specificity (Maly et al. (1996) *Cell* 86: 643-653; Chui et al. (1997) *Cell* 90: 157-167; Hennet et al. (1998) *Proc. Nat'l. Acad. Sci. USA* 95: 4504-4509), and C2 GlcNAcT appears to be dedicated to a role involving selectin-mediated responses of myeloid cells.

A. Core 2 Oligosaccharides in the Biosynthesis of Selectin Ligands

C2 GlcNAcT operates differentially in E-, L- and P-selectin ligand formation. The deficiency of E- and P-selectin-Ig binding to core 2 O-glycan deficient leukocytes observed by flow cytometry was tempered by data from neutrophil rolling assays which revealed significant residual binding on both E- and P-selectin substrates. Additionally, a small amount of L-selectin binding remained in comparison to FucT-VII null leukocytes, but only at the lowest shear forces applied. All three selectins can bind to PSGL-1 and it is possible that PSGL-1 acts as the major selectin counter-receptor in the rolling assay. Residual E- and P-selectin binding by C2 GlcNAcT deficient leukocytes indicates a possible role for N-glycans in physiologic selectin ligand formation. The CD24 glycoprotein is extensively N-glycosylated on myeloid cell surfaces where it has been reported to mediate binding of monocytes and neutrophils to P-selectin (Aigner et al. (1995) *Int. Immunol.* 7: 1557-1565). In addition, the E-selectin counter-receptor, ESL-1 contains only N-linked oligosaccharides and has been found on leukocyte microvilli where it may regulate initial cell adhesion events (Steegmaier et al. (1997) *J. Cell. Sci.* 110: 687-94). Leukocyte L-selectin ligand production appears to be greatly dependent upon core 2 oligosaccharide formation, which may be particularly relevant in secondary interactions involving neutrophil-neutrophil binding at sites of inflammation and extravasation (Walcheck et al. (1996) *J. Clin. Invest.* 98: 1081-7). Our studies indicate that although C2 GlcNAcT provides a significant proportion of E-, L- and P-selectin ligands on leukocytes, it is not as essential as is FucT-VII. Therefore other oligosaccharide substrates of FucT-VII that are not produced by C2 GlcNAcT are also involved in selectin ligand biosynthesis.

B. The Physiologic and Cell-Type-Specificity of C2 GlcNAcT among Leukocytes

With E- and P-selectin binding evident in shear flow studies of C2 GlcNAcT null neutrophils, the decrease observed in neutrophil recruitment during peritoneal inflammation was surprisingly severe. The extent of the reduction is similar to that observed in the absence of FucT-VII with an 80% reduction in neutrophil recruitment. Not all neutrophil recruitment to inflamed peritoneum requires selectins or FucT-VII. Approximately 20% of neutrophils recruited during the first four hours of acute inflammation may be accounted for by the function of the intercellular adhesion molecule-1 (ICAM-1; Kunkel et al. (1996) *J. Exp. Med.* 183: 57-65). These findings imply that selectin and FucT-VII involvement in acute inflammation are dependent upon C2 GlcNAcT and core 2 oligosaccharides.

Altered leukocyte homeostasis in C2 GlcNAcT deficient mice is intermediate in severity in comparison to studies of P-selectin and FucT-VII deficiencies. The major hemodynamic effect in the absence of C2 GlcNAcT was an increase in neutrophil levels. An absence of P-selectin results in a small increase in peripheral neutrophils, but no change in total leukocytes (Mayadas et al. (1993) *Cell* 74: 541-554), whereas mice deficient in either E- or L-selectin exhibit normal peripheral hematologic profiles (Arbones et al. (1994) *Immunity* 1: 247-260; Labow et al. (1995) *Immunity* 1: 709-720). When both P- and E-selectins are missing (Frenette et al., 1996) or in the absence of FucT-VII (Maly et al. (1996) *Cell* 86: 643-653), marked increases in leukocytes are observed, above that measured in C2 GlcNAcT deficient mice. Bone marrow progenitor frequencies were unaltered in C2 GlcNAcT deficient mice, suggesting an increase in neutrophil half-life may account for the neutrophilia as was reported with P-selectin deficiency (Johnson et al. (1995) *Blood* 86: 1106-14). In contrast to results reported in the absence of P-selectin, C2 GlcNAcT deficient mice exhibited a normal bleeding time (Subramaniam et al. (1996) *Blood* 87: 1238-1242; data not shown).

The selective nature of C2 GlcNAcT function was further evident from studies of lymph node morphology and lymphocyte homing. The partial deficit observed in L-selectin binding to lymph node HEVs appeared inconsequential as lymphocyte abundance and homing was not affected. Perhaps physiologic L-selectin ligands are normally expressed in over-abundance and the quantity remaining in C2 GlcNAcT deficient mice is sufficient to facilitate normal lymphocyte homing. It is also possible that the HEV glycoproteins modified by C2 GlcNAcT to carry L-selectin ligands do not participate in lymphocyte homing. As L-selectin ligands may exist on separate oligosaccharide classes (N-glycans, O-glycans, glycolipids, etc.), the underlying structures in these classes may influence their presentation and the efficacy of function in binding L-selectin in vivo. L-selectin counter-receptors implicated in lymphocyte homing include sialylated mucins such as CD34. Their identity is uncertain and CD34 deficient mice exhibit normal lymphocyte homing (Cheng et al. (1996) *Blood* 87: 479-90; Suzuki et al. (1996) *Blood* 87: 3550-62). A possibility that other oligosaccharide classes are involved is consistent with the observation that O-sialoglycoprotease-resistant L-selectin ligands exist on lymph node HEVs (Clark et al. (1998) *J. Cell. Biol.* 140: 721-31). While the structural features of physiologic L-selectin ligands remain to be fully established, the oligosaccharides involved in lymphocyte homing are dependent upon the function of FucT-VII but do not require C2 GlcNAcT, and thus may not be composed of core 2 oligosaccharides.

C. C2 GlcNAcT in Oligosaccharide Diversification and Function

The C2 GlcNAcT glycosyltransferase is essential for generating core 2 O-glycans in the kidney, bone marrow and peripheral leukocytes. Since C2 GlcNAcT can also act on glycolipid substrates (Piller et al. (1984) *J. Biol. Chem.* 259: 13385-90), it is possible that the phenotypes manifested may be due in part to a deficiency of specific glycolipids that are substrates of C2 GlcNAcT in the Golgi. We also cannot rule out the possibility that a distinct gene product encoding a C2 GlcNAcT isozyme is expressed in specific compartments such as lymph node HEVs and which may account for functional L-selectin ligand formation. Several studies have suggested the presence of such an isozyme in mucin producing tissues that is capable of synthesizing both core 2 and core 4 O-glycans (Kuhns et al. (1993) *Glycoconj. J.* 10: 381-94; Ropp et al. (1991) *J. Biol. Chem.* 266: 23863-71). Although core 4 O-glycans may partially compensate for C2 GlcNAcT deficiency, C4 GlcNAcT activity is not normally found in myeloid cell types (Bierhuizen and Fukuda (1992) *Proc. Nat'l. Acad. Sci. USA* 89: 9326-9330; Schachter and Brockhausen (1989) *Symp. Soc. Exp. Biol.* 43: 1-26), and core 4 activity was not induced in tissues from C2 GlcNAcT deficient mice (data not shown).

explain how the C2 GlcNAcT glycosyltransferase selectively regulates myeloid homeostasis and inflammation.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

SEQUENCE LISTING

```
<160> NUMBER OF SEQ ID NOS: 3

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence:wild type C2
      GlcNAcT allele PCR primer W5'

<400> SEQUENCE: 1
gggttacgga tgagctctgt gtc                                              23

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence:wild type C2
      GlcNAcT allele PCR primer W3'

<400> SEQUENCE: 2
ccctggaagc aggacaattc tg                                               22

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence:mutant C2
      GlcNAcT allele loxP primer M3'

<400> SEQUENCE: 3
ctcgaattga tccccgggta c                                                21
```

The function of C2 GlcNAcT in neutrophil recruitment during inflammation is consistent with a role in the biosynthesis of selectin ligands. E-, L- and P-selectin ligand production is only partially C2 GlcNAcT-dependent, yet this partial dependence encompasses a potent and restricted physiologic activity. Inhibition of C2 GlcNAcT activity might provide a selective means to dampen acute inflammatory responses and reperfusion injury (Lowe and Ward (1997) *J. Clin. Invest.* 99: 822-826). Our results imply that core 2 O-glycans provide an unexpectedly restricted biological function that may reflect the presence of additional glycosyltransferases with overlapping activities. The unique modulatory roles exerted by glycosyltransferases may arise through differential expression patterns that can affect levels of oligosaccharides and their structural presentation by core and glycoprotein components. Either possibility may

What is claimed is:

1. A method of inhibiting an inflammatory response in a mammal, the method comprising administering to the mammal a compound that is an analog of a core 2 GlcNAc transferase acceptor substrate and inhibits the activity of the core 2 GlcNAc transferase, thereby inhibiting the inflammatory response in the mammal.

2. The method of claim 1, wherein the inflammatory response is associated with an acute inflammatory disease.

3. The method of claim 2, wherein the acute inflammatory disease selected from the group consisting of appendicitis, tonsillitis, delayed hypersensitivity reactions, inflammation due to sepsis, cutaneous inflammation and ischemic reperfusion injury.

4. The method of claim 1, wherein the inflammatory response is associated with a chronic inflammatory disease.

5. The method of claim 4, wherein the chronic inflammatory disease is rheumatoid arthritis.

6. The method of claim 1, wherein the compound is administered parenterally.

7. The method of claim 1, wherein the inhibition of activity of the core 2 GlcNAc transferase is determined by measuring core 2 GlcNAc transferase activity in a sample from the patient.

8. The method of claim 1, wherein the inhibition of activity of the core 2 GlcNAc transferase is determined by measuring the amount of core 2 glycans in a sample from the patient.

9. A method of inhibiting binding of a first myeloid cell to an endothelial cell or to a second myeloid cell, the method comprising contacting the first myeloid cell with a compound that is an analog of a core 2 GlcNAc transferase acceptor substrate and inhibits the core 2 GlcNAc transferase, thereby inhibiting synthesis of a core 2 oligosaccharide.

10. The method of claim 9, wherein the first myeloid cell is present in a mammal.

11. The method of claim 9, wherein the first myeloid cell is selected from the group consisting of neutrophils, eosinophils, monocytes, and granulocytes.

12. The method of claim 9, wherein the binding of the first myeloid cell to the endothelial cell or to the second myeloid cell is inhibited.

* * * * *

UNITED STATES PATENT AND TRADEMARK OFFICE
CERTIFICATE OF CORRECTION

PATENT NO.         : 7,256,171 B1
APPLICATION NO.    : 09/856391
DATED              : August 14, 2007
INVENTOR(S)        : Jamey D. Marth et al.

Page 1 of 1

It is certified that error appears in the above-identified patent and that said Letters Patent is hereby corrected as shown below:

On the Title Page (54) title please change:

"USE OF CORE 2 G1CNAC TRANSFERASE INHIBITORS IN TREATING INFLAMMATION" to -- USE OF CORE 2 GlcNAc TRANSFERASE INHIBITORS IN TREATING INFLAMMATION --

Signed and Sealed this

Twenty-second Day of January, 2008

JON W. DUDAS
*Director of the United States Patent and Trademark Office*